United States Patent
Push et al.

(10) Patent No.: US 12,233,173 B2
(45) Date of Patent: Feb. 25, 2025

(54) LIGHT-COUPLING CAP STERILIZATION SYSTEM

(71) Applicant: UV Light Care, Inc., Boston, MA (US)

(72) Inventors: Adam Push, Boston, MA (US); Bret Siarkowski, Marlborough, MA (US)

(73) Assignee: UV Light Care, Inc., Boston, MA (US)

( * ) Notice: Subject to any disclaimer, the term of this patent is extended or adjusted under 35 U.S.C. 154(b) by 190 days.

(21) Appl. No.: 17/151,193

(22) Filed: Jan. 17, 2021

(65) Prior Publication Data

US 2021/0244835 A1    Aug. 12, 2021

Related U.S. Application Data

(60) Provisional application No. 62/962,919, filed on Jan. 17, 2020.

(51) Int. Cl.
A61L 2/10    (2006.01)
A61L 2/26    (2006.01)

(52) U.S. Cl.
CPC ............... *A61L 2/10* (2013.01); *A61L 2/26* (2013.01); *A61L 2202/11* (2013.01); *A61L 2202/14* (2013.01); *A61L 2202/24* (2013.01)

(58) Field of Classification Search
CPC ..... A61L 2/10; A61L 2/24; A61L 2/26; A61L 2/28; A61L 2202/11; A61L 2202/14;
(Continued)

(56) References Cited

U.S. PATENT DOCUMENTS 4,266,815 A    5/1981  Cross
4,778,447 A    10/1988 Velde
(Continued)

FOREIGN PATENT DOCUMENTS

CN    1072971 C       10/2001
CN    110997016 B     8/2021
(Continued)

OTHER PUBLICATIONS

B. Liptak, A. Brodgesell, M.F. Hordeski, "Instrument Engineer's Handbook", Fourth Edition, vol. 1, Chapter 7.14, p. 1009 (Year: 2003).*
Jim Blom, "Button and Switch Basics", sparkfun, May 8, 2013 (Year: 2013).*
"Photolyase", "https://en.widipedia.org/w/index.php?title=Photolyase &oldid=684658970", Oct. 8, 2015, pp. 1-4 Publisher: Wikipedia, Published in: US.
(Continued)

*Primary Examiner* — Jennifer Wecker
*Assistant Examiner* — Brady C Pilsbury
(74) *Attorney, Agent, or Firm* — Loginov & Associates, PLLC; William A. Loginov

(57) ABSTRACT

A light-coupling cap can sterilize targets including connectors and other devices such as catheters with Luer fittings conforming to ISO 594 or ISO 80369 standards. The cap can be disposable. A light-coupling cap can reversibly attach to a connector of a target, creating a physical seal and barrier between the inside of the connector and the outside environment while at the same time transmitting light into the connector. A sterilizer can be connected to the end cap while the end cap is connected to the target. The sterilizer can include a UV light emitter that emits UV light through the end cap into the target. The light-coupling end cap sterilization system can be self-healing by measuring internal performance indicators and adjusting its operation in response to them. The light-coupling end cap sterilization system can provide to the user an indication of the amount of light dosage applied to the target.

14 Claims, 29 Drawing Sheets

(58) Field of Classification Search
CPC ............ A61L 2202/16; A61L 2202/24; A61L 2202/122; A61L 2202/123
See application file for complete search history.

(56) References Cited

U.S. PATENT DOCUMENTS

| | | | |
|---|---|---|---|
| 4,816,145 A | 3/1989 | Goudy, Jr. | |
| 5,637,877 A | 6/1997 | Sinofsky | |
| 6,403,030 B1 | 6/2002 | Horton | |
| 6,447,720 B1 | 9/2002 | Horton | |
| 6,447,721 B1 | 9/2002 | Horton | |
| 6,454,937 B1 | 9/2002 | Horton | |
| 6,461,569 B1 | 10/2002 | Boudreaux | |
| 6,524,529 B1 | 2/2003 | Horton | |
| 6,541,777 B1 | 4/2003 | Lombardo | |
| 6,558,410 B1 | 5/2003 | Horton | |
| 6,579,916 B1 | 6/2003 | Askill | |
| 6,730,265 B2 | 5/2004 | Horton | |
| 6,737,020 B1 | 5/2004 | Horton | |
| 6,766,097 B2 | 7/2004 | Horton | |
| 7,420,183 B2 | 9/2008 | Kaiser | |
| 7,612,492 B2 | 11/2009 | Lestician | |
| 7,834,328 B2 | 11/2010 | Redmond | |
| 7,888,657 B1 | 2/2011 | Zadro | |
| 7,950,818 B2 | 5/2011 | Klipstein | |
| 8,197,087 B2 | 6/2012 | Sobue | |
| 8,388,167 B2 | 3/2013 | Klipstein | |
| 8,469,545 B2 | 6/2013 | Sobue | |
| 8,556,950 B2 | 10/2013 | Rioux | |
| 8,574,490 B2 | 11/2013 | Haytman | |
| 8,585,681 B2 | 11/2013 | Boenig | |
| 8,779,386 B2 | 7/2014 | Bak | |
| 9,295,742 B2 | 3/2016 | Rasooly | |
| 2002/0063954 A1 | 5/2002 | Horton | |
| 2003/0017073 A1 | 1/2003 | Eckhardt | |
| 2003/0086817 A1 | 5/2003 | Horton | |
| 2005/0244126 A1 | 11/2005 | Howard | |
| 2006/0195165 A1 | 8/2006 | Gertner | |
| 2007/0176117 A1 | 8/2007 | Redmond | |
| 2008/0027399 A1 | 1/2008 | Harding | |
| 2008/0051736 A1 | 2/2008 | Rioux | |
| 2008/0191466 A1 | 8/2008 | Knipple | |
| 2008/0306454 A1 | 12/2008 | Sikora | |
| 2009/0012459 A1 | 1/2009 | Sobue | |
| 2009/0250626 A1 | 10/2009 | Schlesser | |
| 2011/0085936 A1* | 4/2011 | Haytman | A61L 2/084 250/492.1 |
| 2011/0184382 A1 | 7/2011 | Cady | |
| 2011/0213339 A1 | 9/2011 | Bak | |
| 2012/0053512 A1 | 3/2012 | Muse | |
| 2012/0161032 A1 | 6/2012 | Arcand | |
| 2012/0321509 A1 | 12/2012 | Bak | |
| 2013/0210069 A1* | 8/2013 | Pederson | A61L 2/28 435/288.7 |
| 2013/0211248 A1* | 8/2013 | Cowan | A61M 5/148 600/432 |
| 2013/0267888 A1 | 10/2013 | Rhodes | |
| 2013/0323119 A1 | 12/2013 | Alwan | |
| 2013/0323120 A1 | 12/2013 | Ma | |
| 2014/0066703 A1 | 3/2014 | Blumenkranz | |
| 2014/0140888 A1 | 5/2014 | Neister | |
| 2014/0205498 A1 | 7/2014 | Bak | |
| 2014/0209923 A1 | 7/2014 | Xie | |
| 2014/0264074 A1 | 9/2014 | Victor | |
| 2014/0334974 A1 | 11/2014 | Rasooly | |
| 2014/0341777 A1 | 11/2014 | Deshays | |
| 2015/0100053 A1* | 4/2015 | Livneh | A61B 18/1482 606/34 |
| 2015/0165185 A1 | 6/2015 | Cohen | |
| 2015/0231287 A1 | 8/2015 | Lin | |
| 2015/0231309 A1 | 8/2015 | Bihlmaier | |
| 2015/0290347 A1 | 10/2015 | Braden | |
| 2015/0352348 A1 | 12/2015 | Murphy-Chutorian | |
| 2016/0077292 A1 | 3/2016 | Dobrinsky | |
| 2016/0082138 A1 | 3/2016 | Kermode | |
| 2017/0072077 A1 | 3/2017 | Baker | |
| 2017/0119915 A1 | 5/2017 | Lin | |
| 2017/0232123 A1 | 8/2017 | Burapachaisri | |
| 2018/0369432 A1* | 12/2018 | Zaborsky | G02B 6/02 |
| 2018/0369560 A1* | 12/2018 | Ball | G02B 6/0096 |
| 2019/0290791 A1* | 9/2019 | Baker | A61B 90/70 |
| 2020/0268921 A1* | 8/2020 | Lepine | A61L 2/08 |
| 2021/0113725 A1* | 4/2021 | Etter | A61L 2/10 |

FOREIGN PATENT DOCUMENTS

| | | |
|---|---|---|
| EP | 2161040 A1 | 3/2010 |
| EP | 2231203 B1 | 2/2014 |
| JP | H08266595 A | 10/1996 |
| WO | 2002102421 A1 | 12/2002 |
| WO | 2008014437 A2 | 1/2008 |
| WO | 2007134066 A3 | 10/2008 |
| WO | 2010023329 A1 | 3/2010 |
| WO | 2011107540 A1 | 9/2011 |
| WO | 2013023666 A1 | 2/2013 |
| WO | 2016149645 A1 | 9/2016 |
| WO | 2018013581 | 1/2018 |
| WO | 2018237119 A1 | 12/2018 |

OTHER PUBLICATIONS

Aihara, et al., "Simultaneous Irradiation With Different Wavelengths of Ultraviolet Light Has Synergistic Bactericidal Effect On Vibrio Parahaemolyticus", "Photochemistry and Photobiology", Apr. 17, 2014, pp. 1-38, Publisher: American Society of Photobiology, Published in: USA.

Bak, et al., "A Prototype Catheter Designed for Ultraviolet C Disinfection", "Journal of Hospital Infection", Mar. 3, 2013, pp. 173-177, vol. 84, Publisher: Elsevier, Published in: USA.

Bak, et al., "A UVC Device for Intro-Luminal Disinfection of Catheters: in Vitro Tests On Soft Polymer Tubes Contaminated With Pseudomonas Aeruginosa, Staphylococcus aureus, Escherichia coli and Candida Albicans", "Photochemisty and Photobiology", Jun. 8, 2011, pp. 1123-1128, vol. 87, Publisher: The American Society of Photobiology, Published in: USA.

Bak, et al., "Disinfection of Pseudomonas Aeruginosa Biofilm Contaminated Tube Lumens With Ultraviolet C Light Emitting Diodes", "Biofouling", Oct. 15, 2009, pp. 31-38, vol. 26, No. 1, Publisher: Taylor & Francis, Published in: UK.

Bak, et al., "Dose Requirements for UVC Disinfection of Catheter Biofilms", "Biofouling", Jan. 29, 2009, pp. 289-296, vol. 25, No. 3, Publisher: Taylor & Francis, Published in: UK.

Bak, et al., "Potential in Vivo UVC Disinfction of Catheter Lumens: Estimation of the Doses Received by the Blood Flow Outside the Catheter Tip Hole", "Photochemistry and Photobiology", Dec. 20, 2010, pp. 350-356, vol. 87, Publisher: The American Society of Photobiology, Published in: USA.

Bak, et al., "UVC Fluencies for Preventative Treatment of Pseudomonas Aeruginosa Contaminated Polymer Tubes", "Biofouling", Sep. 20, 2010, pp. 821-828, vol. 26, No. 7, Publisher: Taylor & Francis, Published in: UK.

Bialka, et al., "Efficacy of Pulsed UV-Light for the Decontamination of Escherichia coli 0157:H7 and Salmonella Spp. on Raspberries and Strawberries", "Food Microbiology and Safety", 2008, pp. M201-M207, vol. 73, No. 5, Publisher: Journal of Food Science, Published in: USA.

Bosschaart, et al., "A Literature Review and Novel Theoretical Approach on the Optical Properties of Whole Blood", "Lasers Med Sci", Oct. 12, 2013, pp. 453-479, vol. 29, Publisher: Springer Published in: DE.

Cabiscol, et al., "Oxidative Stress in Bacteria and Protein Damage by Reactive Oxygen 3pecies", "Internatl Microbiol", 2000, pp. 3-8, vol. 3, Publisher: Springer-Verlag Iberica, Published in: DE.

Cadet, et al., "Ultraviolet Radiation-Mediated Damage to Cellular DNA", "Mutation Research", Jan. 26, 2005, pp. 3-17, vol. 571, Publisher: Elsevier B.V., Published in: NL.

Carletti, et al., "Flavonoids and Melanins: a Common Strategy Across Two Kingdoms", International Journal of Biological Sci-

(56) References Cited

OTHER PUBLICATIONS ences, Oct. 29, 2014, pp. 1159-1170, vol. 10, No. 10, Publisher: Ivyspring International Publisher, Published in: AU.

Cassarly, "Recent Advances in Mixing Rods", "Illumination Optics", 2008, pp. 710307-1-710307-10, vol. 7103, Publisher: SPIE, Published in: USA.

Cheng, et al., "Irradiance Formations in Hollow Straight Light Pipes With Square and Circular Shapes", "J. Opt. Soc. Am. A", Feb. 2006, pp. 427-434, vol. 23, No. 2, Publisher: Optical Society of America, Published in: USA.

Cheng, et al., "Irradiance Formations of on-Axis Lam Bert Ian Pointlike Sources in Polygonal Total-Internal-Reflection Straight Light Pipes", "J. Op. Soc. Am. A", Sep. 2007, pp. 2748-2757, vol. 24, No. 9, Publisher: Optical Society of America, Published in: USA.

Dai, et al., "Ultraviolet-C Irradiation for Prevention of Central Venous Catheter-Related Infections: an in Vitro Study", "Photochemistry and Photobiology", 2011, pp. 250-255, vol. 87, Publisher: The American Society of Photobiology, Published in: USA.

Ehling-Schultz, et al., "UV Protection in Cyanobacteria", "European Journal of Phycology", Jun. 3, 2010, pp. 329-338, vol. 34, Publisher: Taylor & Francis, Published in: EP.

Esparza, "Color Patterns in a Tapered Lightpipe With RGB LEDs", "Current Developments in Lens Design and Optical Engineering XI; Advances in Thin Film Coatings VI", 2010, pp. 778601-1-778601-7, vol. 7786, Publisher: SPIE, Published in: USA.

French, et al., "Optical Properties of Materials for Concentrator Photovoltaic Systems", 2009, pp. 000394-000399, Publisher: IEEE, Published in: USA.

Hassett, et al., "Bacterial Adaptation to Oxidative Stress: Implications for Pathogenesis and Interaction With Phagocytic Cells", Dec. 1989, pp. 2574-2582, vol. 3, Publisher: The FASEB Journal, Published in: USA.

Hijnen, et al., "Inactivation Credit of UV Radiation for Viruses, Bacteria and Protozoan (OO) Cysts in Water: a Review", "Water Research", Oct. 26, 2005, pp. 3-22, vol. 40, Publisher: Elsevier Ltd., Published in: NL.

Jori, et al., "Photodynamic Therapy in the Treatment of Microbial Infections: Basic Principles and Perspective Applications", "Lasers in Surgery and Medicine", Jun. 19, 2006, pp. 468-481, vol. 38, Publisher: Wiley InterScience, Published in: USA.

Kari, et al., "Reliability of Point Source Approximations in Compact LED Lens Designs", "Optics Express", Nov. 7, 2011, pp. A1190-A1195, vol. 19, No. S6, Published in: USA.

Kowalski, "UVGI Disinfection Theory", "Ultraviolet Germicidal Irradiation Handbook", 2009, pp. 17-50, Publisher: Springer-Verlag Berlin Heidelberg, Published in: DE.

Liu et al., "Color Me Bad: Microbial Pigments as Virulence Factors", "Cell Press", 2009, pp. 406-413, vol. 17, No. 9, Publisher: Elsevier Ltd., Published in: NL.

Liu, et al., "*Staphylococcus aureus* Golden Pigment Impairs Neotrophil Killing and Promotes Virulence Through Its Antioxidant Activity", "JEM", Jul. 11, 2005, pp. 209-215, vol. 2202, No. 2, Publisher: The Rockefeller University Press, Published in: USA.

Li, et al., "Enhanced Germicidal Effects of Pulsed UV-LED Irradiation on Biofilms", "Journal of Applied Microbiology", Aug. 20, 2010, pp. 2183-2190, vol. 109, Publisher: The Society for Applied Microbiology, Published in: USA.

Lucas-Lledo, et al., "Evolution of Mutation Rates: Phylogenomic Analysis of the Photolyase/Cryptochrome Family", "Society for Molecular Biology and Evolution", Feb. 19, 2009, pp. 1143-1153, vol. 26, No. 5, Publisher: Oxford University Press, Published in: UK.

Moreno, "Output Irradiance of Tapered Lightpipes", "J. Opt. Soc. Am. A", Sep. 2010, pp. 1985-1993, vol. 27, No. 9, Publisher: Optical Society of America, Published in: USA.

Nagae, et al., "Calculation of the Excitation Transfer Matrix Elements Between the S 2 or 3 1 State of Carotenoid and the S 2 or S 1 State of Bacteriochlorophyll", "The Journal of Chemical Physics", Feb. 2, 1993, pp. 8012-8023, vol. 98, Publisher: AIP Publishing, Published in: USA.

Novick, et al., "Experiments on Light-Reactivation of Ultra-Violet Inactivated Bacteria", Aug. 15, 1949, pp. 591-600, vol. 35, No. 1949, Publisher: Genetics, Published in: USA.

Oguma, et al., "Determination of Pyrimidine Dimers in *Escherichia coli* and Cryptosporidium Parvum During UV Light Inactivation, Photoreactivation, and Dark Repair", "Applied and Environmental Microbiology", Oct. 2001, pp. 4630-4367, vol. 67, No. 10, Publisher: American Society for Microbiology, Published in: USA.

Oreski, et al., "Determination of Solar Optical Properties of Transparent Polymer Films Using UV/VIS Spectroscopy", "Solar Energy Materials & Solar Cells", Feb. 6, 2010, pp. 884-891, vol. 94, Publisher: Elsevier B.V., Published in: NL.

Parada, et al., "Effects of MeV Proton Bombardment in Thin Film PFA and FEP Polymers", Surface & Coatings Technology, Sep. 29, 2004, pp. 378-382, vol. 196, Publisher: Elsevier B.V., Published in: NL.

Qiu, et al., "Survival of Shewanella Oneidensis MR-1 After UV Radiation Exposure", "Applied anc Environmental Microbiology", Nov. 2004, pp. 6435-6443, vol. 70, No. 11, Publisher: American Society for Microbiology, Published in: USA.

Ravanat, et al., "Direct and Indirect Effects of UV Radiation on DNA and Its Components", Journal of Photochemistry and Photobiology, Aug. 10, 2001, pp. 88-102, vol. 63, Publisher: Elsevier Science B. V-, Published in: NL.

Ren, et al., "Photo-Oxidation of 6-Thioguanine by UVA: the Formation of Addition Products With Low Molecular Weight Thiol Compounds", "Photochemistry and Photobiology", May 14, 2010, pp. 1038-1045, vol. 86, Publisher: The American Society of Photobiology, Published in: USA.

Roberts, et al., "Recovery From Ultraviolet Irradiation in *Escherichia coli*", Dec. 28, 1948, pp. 363-375, vol. 57, Publisher: Department of Terrestial Magnetism, Carnegie Institute of Washington, Published in: USA.

Sancar, "Structure and Function of DNA Photolyase and Cryptochrome Blue-Light Photoreceptors", "Chem. Rev.", Apr. 19, 2003, pp. 2203-2237, vol. 103, Publisher: American Chemical Society, Published in: USA.

Sanz, et al., "Modelling of Reactivation After UV Disinfection: Effect of UV-C Dose on Subsequent Photoreactivation and Dark Repair", "ScienceDirect", May 25, 2007, pp. 3141-3151, vol. 41, Publisher: Elsevier Inc., Published in: NL.

Saw, "Science Against Microbial Pathogens: Photodynamic Therapy Approaches", 2011, pp. 668-674, Publisher: Formatex, Published in: USA.

Selby, et al., "A Cryptochrome/Photo Lyase Class of Enzymes With Single-Stranged DNA-Specific Photolyase Activity", "PNAS", Nov. 21, 2006, pp. 17696-17700, vol. 103, No. 47, Publisher: The National Academy of Sciences of the USA, Published in: USA.

Siljegovic, et al., "Optical and Dielectric Properties of Fluorinated Ethylene Propylene and Tetrafluoroethylene-Perfluoro(Alkoxy Vinyl Ether) Copolymer Films Modified by Low Energy N4 and C4+ Ion Beams", "Radiation Physics and Chemistry", Aug. 30, 2011, pp. 1378-1385, vol. 80, Publisher: Elsevier Ltd., Published in: NL.

Sinha, et al., "UV-Induced DNA Damage and Repair: a Review", "Photochem. Photobiol. Sci.", Mar. 13, 2002, pp. 225-236, vol. 1, Publisher: The Royal Society of Chemistry and Owner Societies, Published in: UK.

Song, et al, "Application of Ultraviolet Light-Emitting Diodes (UV-LEDs) for Water Disinfection: a Review", "Water Research", Mar. 2, 2016, pp. 341-349, vol. 94, Publisher: Elsevier Ltd., Published in: NL.

Stapleton, et al., "Flavonoids Can Protect Maize DNA From the Induction of Ultraviolet Radiation Damage", "Plant Physiol.", 1994, pp. 881-889, vol. 105, Publisher: American Society of Plant Biologists, Published in: USA.

Sun, et al., "Analysis of the Far-Field Region of LEDs", "Optics Express", Aug. 3, 2009, pp. 13918-13927, vol. 17, No. 16, Published in: USA.

(56) References Cited

OTHER PUBLICATIONS

Sun, et al., "Collimating Lamp With Well Color Mixing of Red/Gree/Blue LEDs", "Optics Express", Jan. 2, 2012, pp. A75-A84, vol. 20, No. S1, Published in: USA.

Tang, et al., "A Comparative in Vitro Photoinactivation Study of Clinical Isolates of Multidrug-Resistant Pathogens", "J. Infect. Chemother.", Apr. 2007, pp. 87-91, vol. 13, No. 2, Publisher: The Japanese Association for Infectious Disease, Published in: JP.

Thiagarajan, et al., "Kinetics of Cyclobutane Thymine Dimer Splitting by DNA Photolyase Directly Monitored in the UV", Jun. 7, 2011, pp. 9402-9407, vol. 108, No. 23, Publisher: PNAS, Published in: USA.

Tyrrell, et al., "Interactions Between UV Radiation of Different Energies IKN the Nactivation of Bacteria", "Journal of Bateriology", Oct. 1978, pp. 437-440, vol. 136, No. 1, Publisher: American Society for Microbiology, Published in: USA.

Vatansever, et al., "Can Biowarfare Agents Be Defeated With Light?", "Virulence", Nov. 15, 2013, pp. 796-825, vol. 4, No. 8, Publisher: Landes Bioscience, Published in: USA.

Venil, et al., "Bacterial Pigments and Their Applications", "Process Biochemistry", Jun. 10, 2013, pp. 1065-1079, vol. 48, Publisher: Elsevier Ltd., Published in: NL.

Wengraitis, et al., "Pulsed UV-C Disinfection of *Escherichia coli* With Light-Emitting Diodes, Emitted at Various Repetition Rates and Duty Cycles", "Photochemistry and Photobiology", 2013, pp. 127-131, vol. 89, Publisher: The American Society of Photobiology, Published in: USA.

Wikipedia, "Carotenoid", "https://en.wikipedia.org/w/index.php?title=Carotenoid&oldid=697884880", Jan. 21, 2016, pp. 1-9, Publisher: Wikipedia, Published in: USA.

Wikipedia, "Flavonoid", "https://en.wikipedia.org/w/index.php?title=Flavonoids&oldid=699998877", Jan. 21, 2016, pp. 1-13, Publisher: Wikipedia, Published in: USA.

Wikipedia, "Ultraviolet Germicidal Irradiation", "https://en.wikipedia.Org/w/index.php?itle=Ultraviolet_germicidal_irradiation&oldid=689183127", Jan. 21, 2016, pp. 1-10, Publisher: Wikipedia, Published in: USA.

Yin, et al., "Light Based Anti-Infectives: Ultraviolet C Irradiation, Photodynamic Therapy, Blue Light, and Beyond", "Current Opinion in Pharmacology", 2013, pp. 731-762, vol. 13, Publisher: Elsevier Ltd., Published in: NL.

Yoshii, et al., "Photo-Excitation of Carotenoids Causes Cytotoxicity via Singlet Oxygen Production", "Biochemical and Biophysical Research Communication", 2012, pp. 640-645, vol. 417, Publisher: Elsevier Inc., Published in: NL.

Zhao, et al., "Reactive Oxygen Species and the Bacterial Response To Lethal Stress", "Curr. Opin. Microbiol.", Oct. 2014, pp. 1-12, Publisher: Elsevier, Ltd., Published in: NL.

Zimmer, et al., "Potential Repair of *Escherichia coli* DNA Following Exposure to UV Radiation From Both Medium- and Low-Pressure UV Sources Used in Drinking Water Treatment", "Applied and Environmental Microbiology", Jul. 2002, pp. 3293-3299, vol. 68, No. 7, Publisher: American Society for Microbiology, Published in: USA.

Arecchi et al., "Mixing rod", field guide to illumination, excerpt . (Year: 2007) 2 pages.

\* cited by examiner

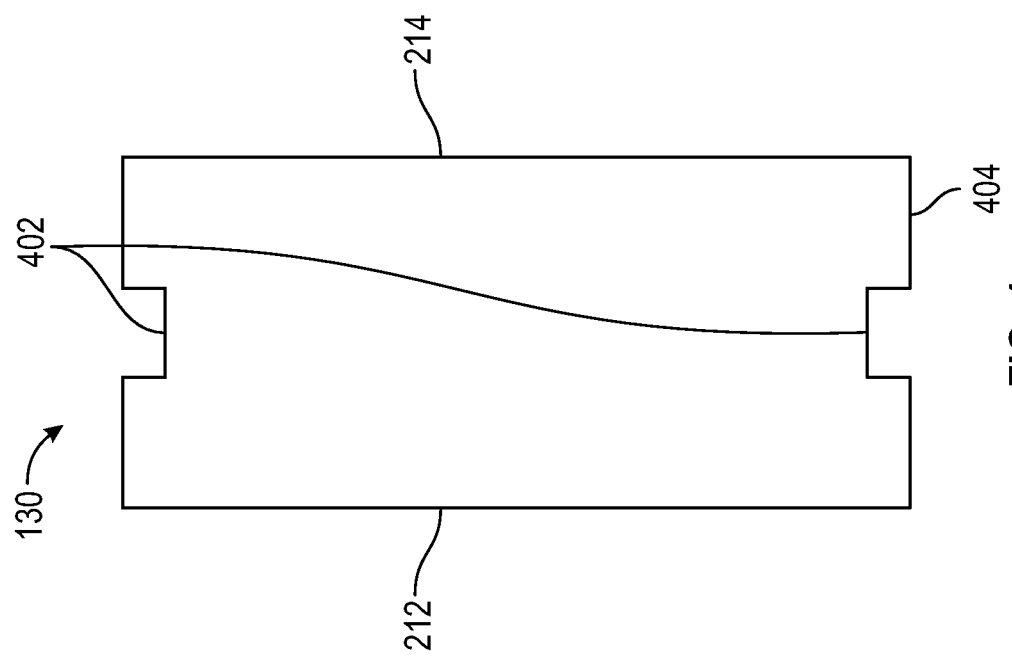

sensing system with a light blocker, according to an illustrative embodiment;
LIGHT-COUPLING CAP STERILIZATION SYSTEM

RELATED APPLICATION

This application claims the benefit of U.S. Provisional Application Ser. No. 62/962,919, entitled LIGHT-COUPLING CAP STERILIZATION SYSTEM, filed Jan. 17, 2020, the teachings of which are expressly incorporated herein by reference.

FIELD OF THE INVENTION

The present disclosure relates to sterilization, and more particularly to sterilization using ultraviolet radiation.

BACKGROUND OF THE INVENTION

Central Venous Catheters (CVCs) are medical devices used to provide access to a patient's bloodstream. CVCs are widely used in many healthcare settings, such as critical care or intensive care units (ICUs) within Acute Care Hospitals (ACHs), outpatient specialty care clinics and hospitals, and home healthcare. There are many applications for CVCs, including parenteral nutrition, chemotherapy, and hemodialysis (HD).

Although widely used and vital to providing health care in many applications, CVCs are prone to infections caused by pathogenic microorganisms colonizing the exterior (extraluminal) and interior (intraluminal) parts of the catheter and migrating to bloodstream-contacting portions of the catheter. Once sufficient numbers of pathogens can enter a patient's bloodstream, Catheter-Related Bloodstream Infections (CRBSIs) can occur. CRBSIs are serious, life-threatening events which can cause great harm to patients and cost hundreds of millions of dollars to healthcare systems across the globe. Improvements in practices such as hand hygiene and aseptic technique have not eliminated the problem. A more effective system for sterilizing CVCs is needed.

SUMMARY OF THE INVENTION

The present invention helps to reduce or eliminate the CRBSI problem by enabling the safe application of ultraviolet (UV) light to the intraluminal part of CVCs and other medical devices, killing microorganisms before they can colonize the medical devices. UV light can kill microorganisms by damaging their DNA through photochemical reactions. Furthermore, disinfection by UV light offers advantages compared to chemical or antibiotic methods of disinfection because it does not carry the patient health risks related to chemical exposure, nor the risk of promoting antibiotic resistance among microorganisms.

In an illustrative embodiment embodiment, a sterilizer cap can include an outer shroud (that can be internally threaded), an inner connector interface (that can be frustoconical in shape), and an optic within the inner connector interface. The inner connector interface can define a hollow inner cavity. Illustratively, the sterilizer cap is adapted to interconnect with a medical device. The medical device can include a Luer fitting and the outer shroud is adapted to engage and lock relative the Luer fitting. One or more light-sensing indicators can receive light from a sterilization system incident on the medical device, and these indicators can comprise a photochromic substance, an irreversible photoreactive substance, a photodiode, a phototransistor, and/or an optical power sensor. The photochromic or irreversible photoreactive chemical substance can be incorporated or embedded into the material of the sterilizer cap. Illustratively, the optic can be operatively connected to a beam splitter that divides light passing through the optic. One or more sensors can be adapted to receive redirected light from the optic and transmit information about the redirected light to one or more processors. The transmitted information can includes at least one of intensity, or radiant flux, or radiant power, or irradiance, or wavelength, and spectral power. A photointerrupter system can detect when the interface is interconnected with a medical device based upon optical transmission of light therebetween.

BRIEF DESCRIPTION OF THE DRAWINGS

The invention description below refers to the accompanying drawings, of which:

FIG. 4 is a partially-cut away view of an optical element with a retainer, according to an illustrative embodiment;

DETAILED DESCRIPTION

A light-coupling end cap can be used on medical devices with connector ports into internal spaces or cavities. By way of non-limiting example, the connector for a connector port can be a Luer fitting as described by the ISO 594 standard. This exemplary Luer fitting can be a female type fitting with external threads (commonly called a "Luer lock" connector). This connector can function as a port for conveying fluids such as water, blood, plasma, nutrients, saline, etc. into or out of a space or cavity within a medical device. That medical device can be, by way of non-limiting example, a tube or catheter with a space or cavity being the lumen of the tube or catheter.

The end cap can have mating features appropriate for securely connecting to the connector port of the device. The end cap can form a physical barrier, or seal, between the device port and the outside environment. At the same time, the end cap can have optically-transparent, or partially transparent, features and surfaces so that light in desired wavebands (by way of non-limiting example, UV-C) can be transmitted through the end cap into the lumen of the port and the internal spaces or cavities of the device, such as the lumen of a tube or catheter if the medical device were a tube or catheter. The end cap can be referred to as a plug, or optical plug, because it can plug into a receiving port and form a physical barrier or seal preventing material such as fluids or solids passing through the port but at the same time can allow light of predetermined wavelengths (such as UV-C, or UV-A, or UV-B) to pass through the port.

The end cap can be called a cap because it can have retaining features such as threads (as in screw threads) or a latch or latches, or other mechanisms or features to provide a retaining force to secure the cap to the mating port. Because the end cap can couple light from an external light source into an internal space of a separate device or object, it can be described as light-coupling and can be called a light-coupling cap, or light-coupling plug, or light-coupling end cap, etc.

The cap can have an internal threaded part or parts to attach to the threaded part or parts of a corresponding mating connector. By way of non-limiting example, the mating connector that can correspond to the cap can be a female Luer lock with external threads.

Figure 1A:
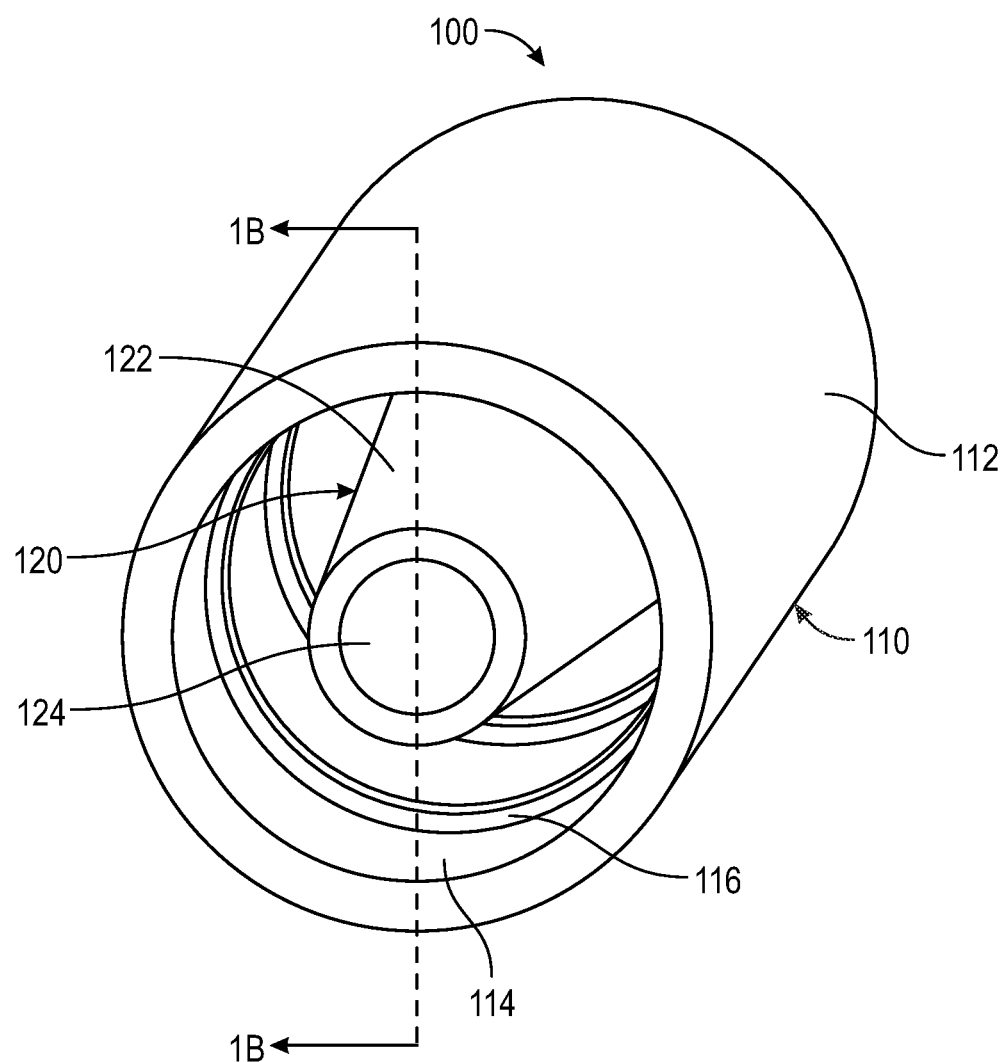
FIG. 1A is a perspective view of a disinfecting cap, according to an illustrative embodiment.
Figure 1B:
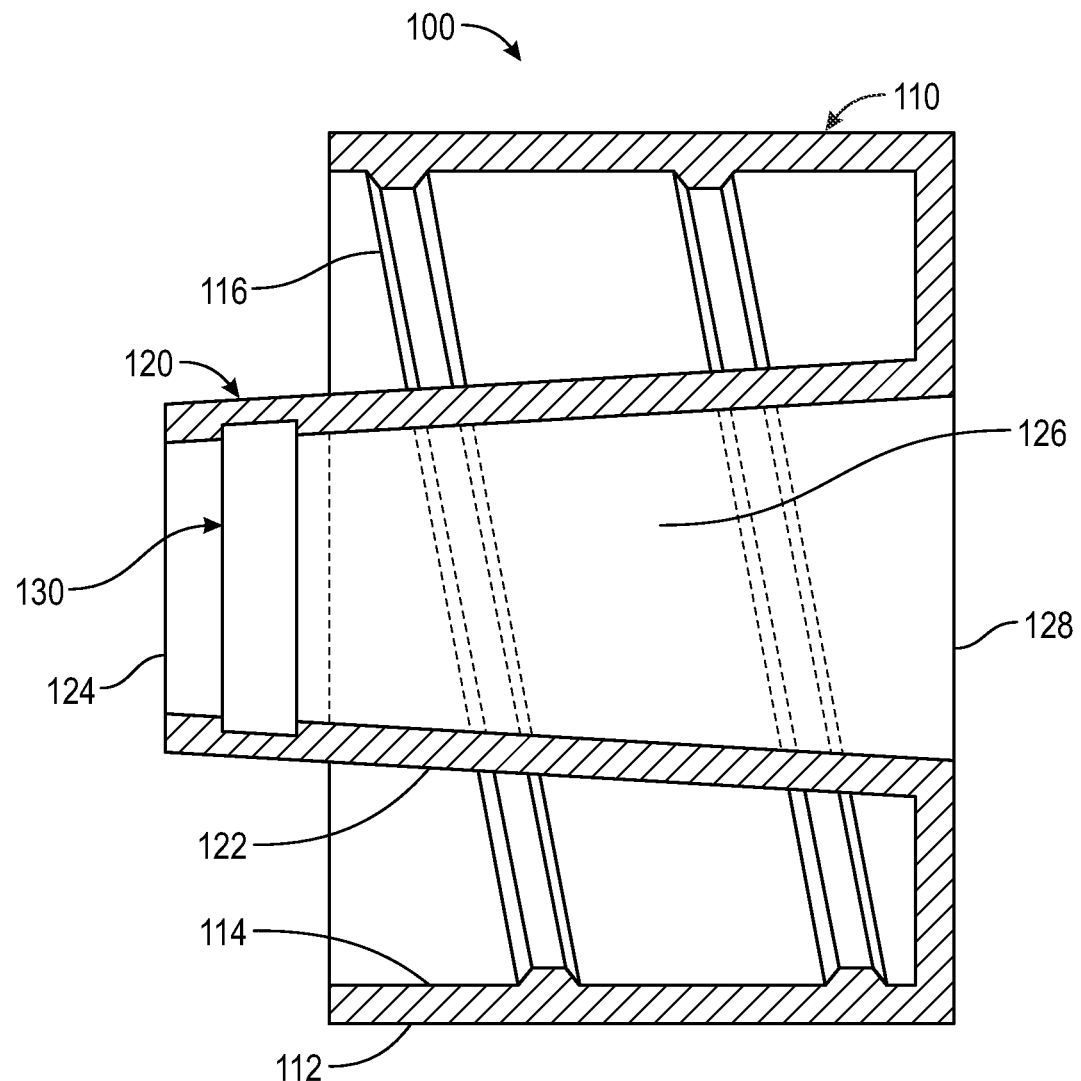
FIG. 1B is a cross-sectional view of the disinfecting cap, taken along cross-section line 1B-1B of FIG. 1A, according to an illustrative embodiment.

FIG. 1A is a perspective view of a disinfecting end cap, according to an illustrative embodiment. A disinfecting end cap 100 can also be referred to as a cap, an end cap, a light coupling cap, a plug, or an optical plug. FIG. 1B is a cross-sectional view of the cap, taken along cross-section line 1B-1B of FIG. 1A, according to an illustrative embodiment. Turning to both FIGS. 1A and 1B, the end cap 100 can have an outer shroud 110 and an inner connector interface 120. The inner connector interface can be a male tapered fitting. The outer shroud 110 and inner connector interface 120 can, alone or in combination, form a connector for mating with a complementary connector on a separate body or device or object. The connector formed by outer shroud 110 and/or inner connector interface 120 alone or in combination can be a Luer type connector as defined by ISO 594 or other standard, or another type of connector. The inner connector interface can be the size and shape of the tapered male portion of a Luer fitting. The outer shroud 110 can protect the inner connector interface 120. The outer shroud 110 can be a structure suitable to allow a user to handle and manipulate the end cap 100. The outer shroud 110 can have an external surface 112 and an internal surface 114. The outer surface 112 can be suitable for handling by a user to manipulate the end cap 110. The outer surface 112 can be textured and/or have various features such as knurls, treads, cavities or ridges to facilitate handling by a user. The inner surface 114 can have attachment features 116, such as screw threads, for securely attaching to a mating connector on a separate body, device, or object. The inner connector interface 120 can have an outer surface 122. The outer surface 122 can be shaped to conform to a standard such as ISO 594 (Luer fitting standard) or another standard. The inner connector interface 120 can have a front portion 124. The end cap can have an optic 130 that can be at the front portion 124 of the inner connector interface 120. Optic 130 can be made from a solid material such as glass, plastic, fused silica, sapphire, or another material. The optic 130 can be a lens, lens array, window, or another type of optic. In various embodiments, the inner connector interface can include an open space at the front portion 124. The inner connector interface 120 can have an inner cavity 126 which can be frustoconical, cylindrical, square, or another shape, and can extend through to the back side of the end cap 100, terminating with a hole 128. The inner cavity 126 can be filled with an optical material such as plastic, fused silica, sapphire, glass, or another type of optical material. The material filling the inner cavity 126 can act as an optic such as a light guide, light pipe, or light homogenizing rod. The inner cavity 126 can be hollow. The inner cavity 126 can have an optic 130 such as a lens, or window, or lens array, or other optic embedded or mounted within it.

In various embodiments, the end cap can be a light-coupling end cap because it can function as a cap, as described above, and at the same time can function as a window allowing light to pass through the cap and into the connector on a medical device. Thus, it can allow light to be coupled from an external light source into the inside space or cavity through a connector port.

In various embodiments, an end cap can conform to the ISO 594 Luer lock male fitting shape. The end cap can be manufactured using an injection molding process. The cap can be made from a plastic resin such as cyclic olefin copolymer (COC). An exemplary COC resin, TOPAS 8007X10, can transmit a significant percentage (40-70%) of UV-C/UV-B light (260-280 nanometer) through the end cap. Furthermore, a fused silica or fused quartz optic 130 can be inserted into the distal end of the inner connector interface 120 to further improve the intensity of the transmitted light, because fused silica/quartz can transmit close to 90% of light incident in the range 260 to 280 nanometer. The optic 130 can be a circular disk or other shape suitable for embedding into the Luer part that can be made from plastic. The optic 130 can be 0.5 mm thick, or 1 mm thick, or another suitable thickness to ensure mechanical strength and provide a physical barrier or seal between the lumen (e.g., catheter lumen) and the outside environment. The interior of the inner connector interface 120 can be a solid, or a hollow cavity filled with air or a fluid such as water. If fluid, the fluid can act as a liquid light pipe and can be sealed at the other end with a second fused silica window or other material. The hollow cavity can contain a solid light pipe made of a material such as fused silica. The internal walls of the hollow cavity can be coated with a reflective material such as aluminum or another material with reflective properties in the desired range of wavelengths appropriate to the application. The reflective coating can convey light from an external light source through the cap and into the inside space or cavity of the mating port to which the cap can be attached.

The hollow cavity can receive a light source from a compatible device, or from a standalone light source. The received light source can be positioned very close to, or abutting, the tip of the inner connector interface, which can increase the intensity of the light emitted through the optic into a space or cavity or surface on the other side of the optic. By way of non-limiting example, the cap can be connected to a connector port of a central venous catheter, and the light from a light source inside the cap's internal cavity can pass through the tip of the end cap, which can include the optic 130. The light can pass through the lumen of the catheter's connector port and through the catheter lumen, and the light can "strike" the interior surfaces of the catheter's connector port and the interior surfaces of the catheter lumen. The received light source can be positioned in a range from approximately 0.5 mm to approximately 10.0 mm from the tip of the Luer fitting. The received light source can be positioned between approximately 0.5 mm and approximately 1.0 cm, between approximately 1.0 mm and approximately 1.5 mm, between approximately 1.5 mm and approximately 2.0 mm, between approximately 2.0 mm and approximately 2.5 mm, between approximately 2.5 mm and approximately 3.0 mm, between approximately 3.0 mm and approximately 3.5 mm, between approximately 3.5 mm and approximately 4.0 mm, between approximately 4.0 mm and approximately 4.5 mm, between approximately 4.5 mm and approximately 5.0 mm, between approximately 5.0 mm and approximately 5.5 mm, between approximately 5.5 mm and approximately 6.0 mm, between approximately 6.0 mm and approximately 6.5 mm, between approximately 6.5 mm and approximately 7.0, between approximately 7.0 mm and approximately 7.5 mm, between approximately 7.5 mm and approximately 8.0 mm, between approximately 8.0 mm and approximately 8.5, between approximately 8.5 mm and approximately 9.0 mm, between approximately 9.0 mm and 9.5 mm, and between approximately 9.5 mm and 10.0 mm from the tip of the Luer fitting.

The optic 130 can be embedded into the end cap as an insert at the time of injection molding or can be inserted after injection molding of the end cap. If inserted after the formation of the end cap, the optic 130 can be retained in place by friction force, or can be retained in place by adhesive or other type of chemical or physical bonding, or can be retained in place by a combination of these methods and/or other methods.

The optic can be inscribed on its circumference with grooves, indentations or other features to allow it to be more securely retained within the plastic part of the assembly. The circumferential edge(s) of the optic 130 can be roughened or modified in a way to aid in sealing and retaining the optic 130 within another body, such as an end cap. The edge modifications can entail a chemical modification to change material properties (such as, by way of non-limiting example, hydrophobicity or hydrophilicity), or it can entail addition of mechanical features such as, by way of non-limiting example, protruding features or recessed features.

Figure 2A:
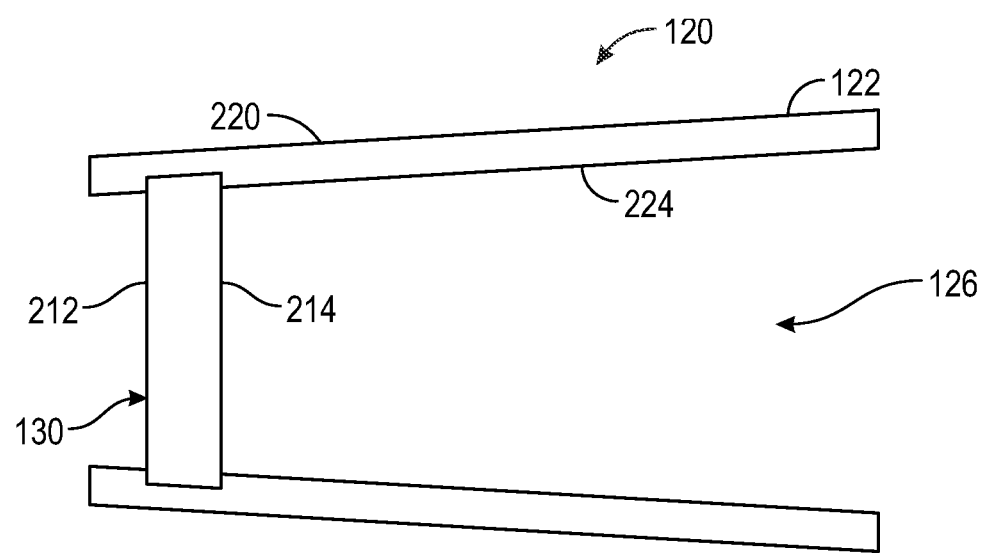
FIG. 2A is a partially cut-away view of an inner connector interface, showing the interior of the inner connector interface, according to an illustrative embodiment.

FIG. 2A is a partially cut-away view of an inner connector interface, showing the interior of the inner connector interface, according to an illustrative embodiment. The inner connector interface can be a male tapered fitting. An inner connector interface 120 can have a body 220 which can be a frustoconical shape. Body 220 can conform to a standard connector specification such as ISO 594 (Luer fitting), or another shape conforming to another standard connector specification, or an arbitrary shape conforming to a proprietary or custom specification. An inner connector interface body 220 can have a frustoconical shape such as a Luer connector conforming to the ISO 594/ISO 80369 standard, but other shapes suitable for connecting with other types of connectors are possible. The inner connector interface body 220 can have an outer surface 122 and an inner surface 224. The inner connector interface body 220 can be made of an injection-moldable plastic material or other material. By way of non-limiting example, the body can be made of cyclic olefin polymer (COP) or copolymer (COC), or can be made of a fluoropolymer, such as fluorinated ethylene propylene (FEP), ethylene tetrafluoroethylene (ETFE), or polyvinylidene fluoride (PVDF) because of the transmissive properties of these materials for UV light. By way of further non-limiting example, the body 220 can be made of PMMA or acrylic. An inner connector interface 120 can have an optic 130. An optic 130 can have an outer surface 212 and an inner surface 214. The optical element 130 can be made of a suitable optical material for transmission, or shaping, or both transmission and shaping, of light of predetermined wavelengths. By way of non-limiting example, the light can be ultraviolet light, visible light, or infrared light. By way of further non-limiting example, the light can be ultraviolet light in the wavelength range 250-290 nm. By way of non-limiting example, optic 130 can be made from an optical material such as glass, fused silica, sapphire, or other optical material. Optical element 130 can be a window, lens, lens array, light pipe, or other optical component. An inner connector interface 120 can have a hollow cavity 126. Optical element 130 can be a separate piece mounted within the body 220 or it can be made from the same material as, and integrated into, the body 220. In various embodiments with a separate optic 130, the optic can be insert-molded or overmolded into the body 220, or mounted using another manufacturing process that forms the body 220 around the optical element 130. In various embodiments, the optical element 130 can be mounted in the body 220 after the body has already been made. The optical element 130 can be attached, or held, or mounted within the body 220 using adhesive, or chemical bonding, or welding, or friction, or retaining features integrated into the end cap body, or by another retaining method.

In various embodiments, the optic 130 can be made from the same material as the body and integrated into the body 220, and the optical element 130 can be formed as a feature of the body 220 during manufacturing of the body. By way of non-limiting example, the optic 130 and body 220 can be formed as a single contiguous piece from a mold in a plastic injection-molding process or other molding process, or a subtractive process such as grinding or cutting, or another manufacturing process. In the embodiment shown in FIG. 2A, the optical element 130 is depicted as being located at one end of the body 220, however, in various embodiments the optical component can be located at any arbitrary location. The inner connector interface body outer surface 122, or inner surface 224, or the optical element outer surface 212, or optical element inner surface 214, or any combination of outer and inner surfaces 122, 224, 212, and 214 can have a surface finish suitable for optical transmission of ultraviolet light or other wavelengths of light. The surface finishes of 122, 224, 212, and/or 214 can be designed for specific optical qualities such as low reflection, low diffusion, low refraction, high transmission, or any other optical characteristic. In various embodiments, the surfaces can have approximately an 80-20 scratch-dig. In various embodiments, the surface can have approximately a 40-20 scratch-dig. In various embodiments, the surface can have approximately a 20-10 scratch-dig. In various embodiments, the surface can have approximately a 10-5 scratch-dig. In various embodiments, the surface finish can be under 100 Angstrom RMS. In various embodiments, the surface finish can be under 50 Angstrom RMS. In various embodiments, the surface finish can be under 20 Angstrom RMS. In various embodiments, the surface finish can be under 5 Angstrom RMS. In various embodiments, some or all of the inner connector interface and/or optic can have an index of refraction that can be approximately 1.4-4.0, similar to general optical glasses. In various embodiments, some or all of the inner connector interface and/or optic can have an index of refraction that can be approximately 1.4. In various embodiments, some or all of the inner connector interface and/or optic can have an index of refraction that can be approximately 1.52, such as NBK7 optical glass at 586 nm. In various embodiments, some or all of the inner connector interface and/or optic can have an index of refraction that can be approximately 1.8. In various embodiments, some or all of the inner connector interface and/or optic can have an index of refraction that can be approximately 1.83, such as sapphire at 265 nm. In various embodiments, some or all of the inner connector interface and/or optic can have an index of refraction that can be approximately 4.0. In various embodiments, some or all of the inner connector interface and/or optic can have an Abbe number of approximately 25-60. In various embodiments, some or all of the inner connector interface and/or optic can have an Abbe number greater than 55. In various embodiments, some or all of the inner connector interface and/or optic can have an Abbe number of approximately 64.17, such as NBK7 optical glass. In various embodiments, some or all of the inner connector interface and/or optic can have an Abbe number of approximately 72.24, such as sapphire.

Figure 2B:
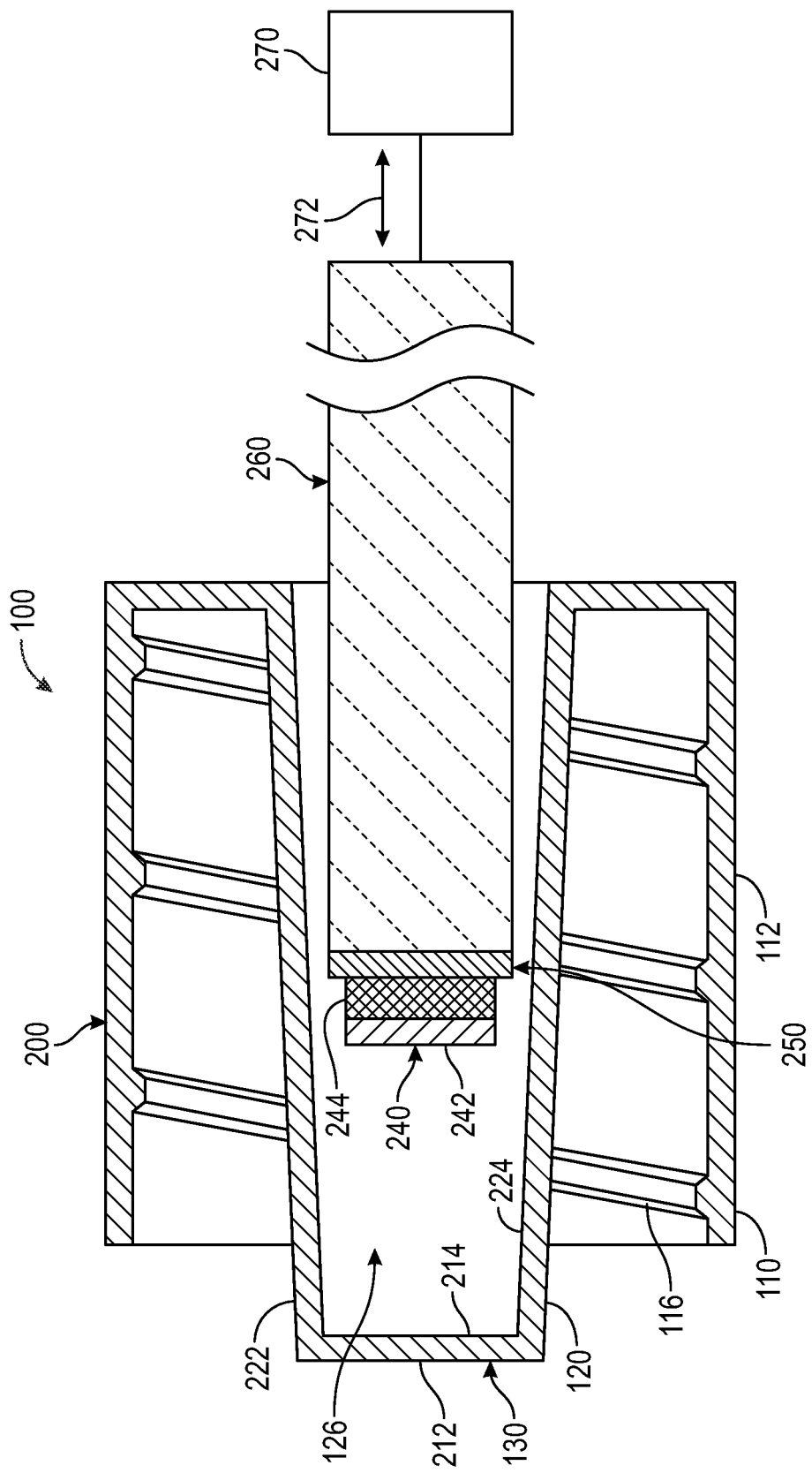
FIG. 2B is partially-cut away view of a cap, showing an inserted light source, according to an illustrative embodiment.

FIG. 2B is a partially-cut away view of a cap, showing an inserted light source, according to another illustrative embodiment. In an embodiment, an external light source 240 can be inserted into internal hollow cavity 126 of the cap 100. The cap 100 can have a cap body 200 that can include the outer shroud 110 and the inner connector interface 120. The cap body 200 can be made of a rigid or semi-rigid material and said material can have optical properties suitable for transmission of light. Cap body 200 can have an external surface 112 and attachment features 116 that can be internal threading. Attachment features 116 can attach to a complementary external threading or tab features on a mating connector. By way of non-limiting example, attachment features 116 can be internal threading that can conform to a connector standard such as ISO 594, or ISO 80369, or another standard. Optic 130 can be unitary with cap body 200. In this embodiment, light source 240 can be inserted into internal hollow cavity 126 of cap body 200. Light source 240 can have a body 244 and an optical component 242 that can be a lens, lens array, or window. By way of non-limiting example, light source 240 can be a light-emitting diode (LED). Light source 240 can be mounted on a platform 250. Light source platform 250 can provide a physical platform to mount and support light source 240, and it can also provide electrical connections for delivering electrical power (current) and other control and communications signals to and from light source 240. By way of non-limiting example, light source platform 250 can be a printed circuit board (PCB). Platform 250 can be attached to a stem 260. Stem 260 can be a circular or rectangular rod, or it can be another shape. Stem 260 can have one or more internal spaces which can contain electrical components, electronics, or mechanical elements which can form various mechanisms, sensors, or other components. By way of further non-limiting example, the stem 260 can have in its internal space(s) electrical wires which can carry electrical current to light source platform 250 or light source 240 or both.

In various embodiments, the stem 260 can be operatively connected to a linear actuator 270 that can move the light source back and forth within the hollow inner cavity 126 in the directions of arrow 272. The linear actuator can be positioned outside of the stem, or can be partially or entirely within the stem 260. The linear actuator can include gears, belts, electromagnets, or other mechanisms within the internal space(s) of the stem 260, or outside of the stem 260, to create a linear motion.

Figure 3A:
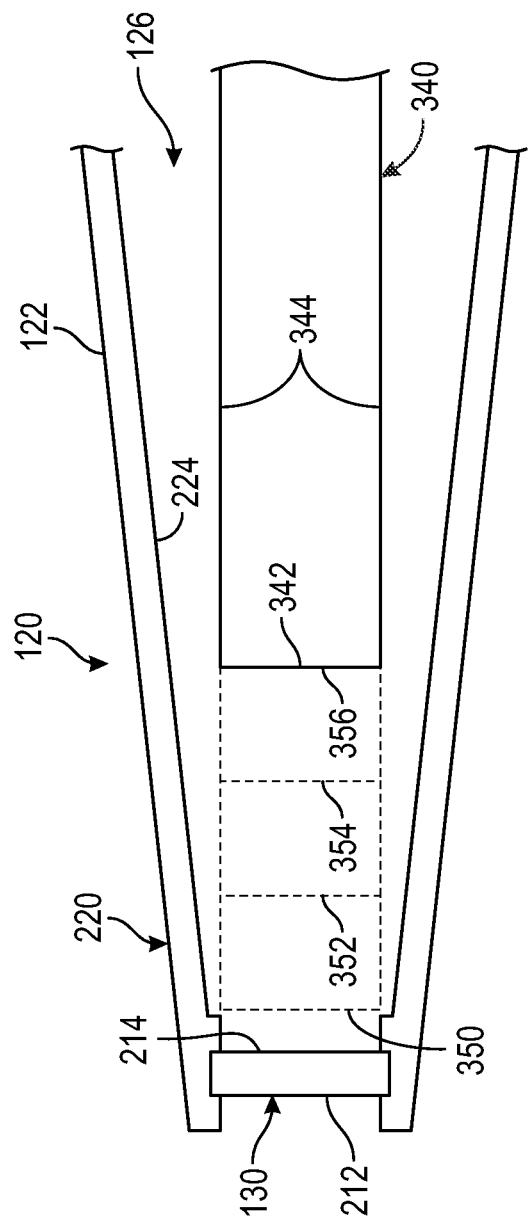
FIG. 3A is a partially-cut away view of an inner connector interface of a cap, showing an inserted light conveyer, according to an illustrative embodiment.

FIG. 3A is a partially-cut away view of an inner connector interface of a cap, showing an inserted light conveyer, according to an illustrative embodiment. An inner connector interface 120 can have a body 220 which can be a frusto-conical shape. Body 220 can conform to a standard connector specification such as ISO 594 (Luer fitting), or another shape conforming to another standard connector specification or an arbitrary shape conforming to a proprietary or custom specification. The inner connector interface body 220 can have a frustoconical shape, but other shapes can also be suitable for connecting with various types of connectors. The inner connector interface body 220 can have an outer surface 122 and an inner surface 224. The inner connector interface body 220 can be made of an injection-moldable plastic material or other material. By way of non-limiting example, the body can be made of cyclic olefin polymer (COP) or copolymer (COC); or can be made of a fluoropolymer, such as fluorinated ethylene propylene (FEP), ethylene tetrafluoroethylene (ETFE), or polyvinylidene fluoride (PVDF) because of the transmissive properties of these materials for UV light. By way of further non-limiting example, the body 220 can be made of PMMA or acrylic. An inner connector interface 120 can have an optic 130. The optic 130 can have an outer surface 212 and an inner surface 214. The optical element 130 can be made of a suitable optical material for transmission, or shaping, or both transmission and shaping, of light of predetermined wavelengths, such as ultraviolet light, visible light, or infrared light. By way of further non-limiting example, the optic 130 can be made from an optical material such as glass, fused silica, sapphire, or other optical material. The optical element 130 can be a window, lens, lens array, light pipe, or other optical component. An inner connector interface 120 can have a hollow cavity 126. The optic 130 can be a separate piece mounted within the body 220 or it can be made from the same material as, and integrated into, the body 220. In various embodiments with a separate optic 130, the optic can be insert-molded or overmolded into the body 220, or mounted using another manufacturing process that forms the body 220 around the optic 130. In various embodiments, the optic 130 can be mounted in the body 220 after the body has already been made. The optic 130 can be attached, or held, or mounted within the body 220 using adhesive, or chemical bonding, or welding, or friction, or retaining features integrated into the end cap body, or by another retaining method.

In FIG. 3A, the optical element 130 is depicted as being located at one end of the body 220, however, in various embodiments the optical component can be located at any arbitrary location. The inner connector interface body outer surface 122, or inner surface 224, or optical element outer surface 212, or inner surface 214, or any combination of outer and inner surfaces 122, 224, 212, and 214 can have a surface finish suitable for optical transmission of ultraviolet light or other wavelengths of light. The surface finishes of 122, 224, 212, and 214 can be designed for specific optical qualities such as low reflection, low diffusion, low refraction, high transmission, or any other optical characteristic. In various embodiments, the surfaces can have approximately an 80-20 scratch-dig. In various embodiments, the surface can have approximately a 40-20 scratch-dig. In various embodiments, the surface can have approximately a 20-10 scratch-dig. In various embodiments, the surface can have approximately a 10-5 scratch-dig. In various embodiments, the surface finish can be under 100 Angstrom RMS. In various embodiments, the surface finish can be under 50 Angstrom RMS. In various embodiments, the surface finish can be under 20 Angstrom RMS. In various embodiments, the surface finish can be under 5 Angstrom RMS. In various embodiments, some or all of the inner connector interface and/or optic can have an index of refraction that can be approximately 1.4-4.0, similar to general optical glasses. In various embodiments, some or all of the inner connector interface and/or optic can have an index of refraction that can be approximately 1.4. In various embodiments, some or all of the inner connector interface and/or optic can have an index of refraction that can be approximately 1.52, such as NBK7 optical glass at 586 nm. In various embodiments, some or all of the inner connector interface and/or optic can have an index of refraction that can be approximately 1.8. In various embodiments, some or all of the inner connector interface and/or optic can have an index of refraction that can be approximately 1.83, such as sapphire at 265 nm. In various embodiments, some or all of the inner connector interface and/or optic can have an index of refraction that can be approximately 4.0. In various embodiments, some or all of the inner connector interface and/or optic can have an Abbe number of approximately 25-60. In various embodiments, some or all of the inner connector interface and/or optic can have an Abbe number greater than 55. In various embodiments, some or all of the inner connector interface and/or optic can have an Abbe number of approximately 64.17, such as NBK7 optical glass. In various embodiments, some or all of the inner connector interface and/or optic can have an Abbe number of approximately 72.24, such as sapphire.

An end cap can have a light conveyer 340 having an end surface 342 and side surfaces 344. The light conveyer 340 can be a lens, a light pipe, a window, a light source, or another type of optical component. A light conveyer can convey light from an external light source into a hollow cavity 126 within the inner connector interface 120. A linear actuator can move the light pipe 340 between various positions, including a fully inserted position 350 and partially inserted positions 352, 354, and 356. In various embodiments, the light conveyer 340 can be positioned statically within the hollow cavity 126, or it can be adjusted dynamically as the system is in operation to change the way the light is emitted into a medical device through the body 220, or through the optic 130, or through both the body and the optic. The position of the distal end of the light conveyer can be chosen to affect how much of the mated female fitting would be exposed to light exiting the light pipe. By way of non-limiting example, if the light conveyer were a light pipe, light can be emitted only through the end surface 342, and therefore the location of the end surface within the hollow cavity would determine the origin point where light would radiate out from within the hollow cavity 126. A cone of light exiting the light pipe would intersect a larger portion of the Luer fitting the farther back the light pipe was from the distal tip of the male Luer fitting. Light conveyer 340 can be made from materials suitable for transmission of predetermined wavelengths of light, such as ultraviolet light, visible light, or infrared light. By way of non-limiting example, the light conveyer 340 can be made from fused silica, sapphire, glass, or another material.

Figure 3B:
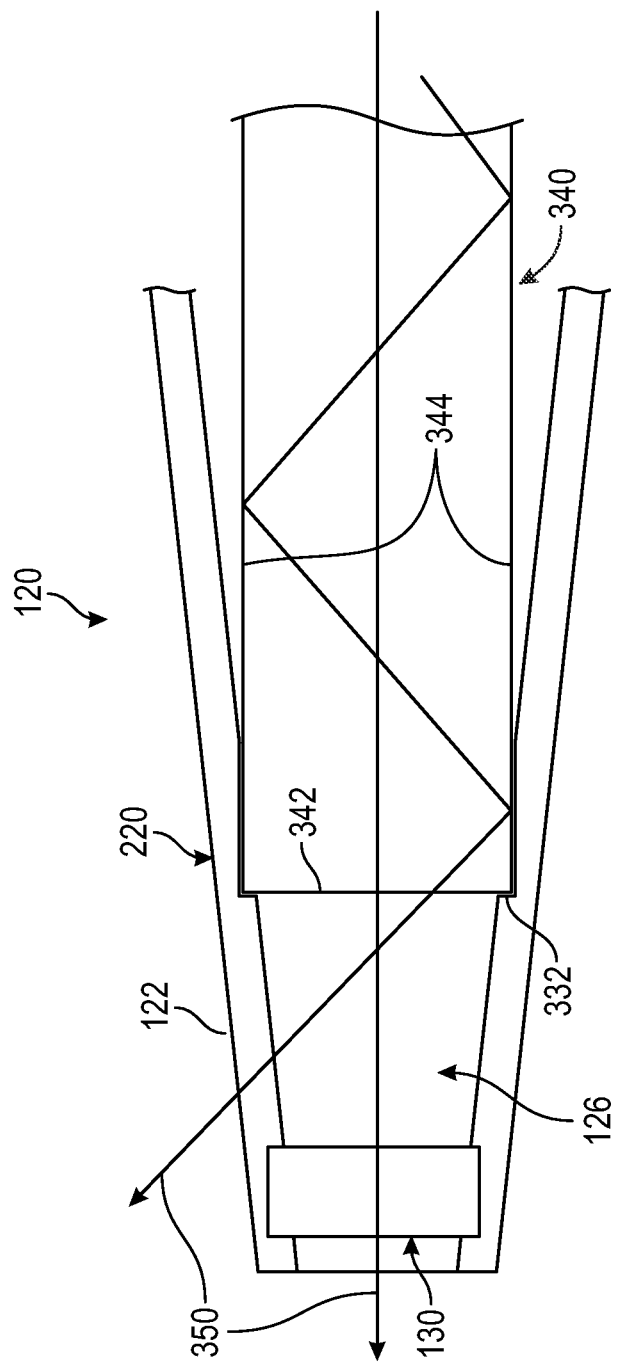
FIG. 3B is a partially-cut away view of an inner connector interface of a cap, showing the inner workings with light rays transmitted through a light conveyer, according to an illustrative embodiment.

FIG. 3B is a partially cut away view of an inner connector interface of a cap, showing the inner workings with light rays transmitted through a light conveyer, according to an illustrative embodiment. A cap can have a light conveyer 340 that can be fixed to the end cap in a fixed position, or can have an adjustable position within the end cap. In various embodiments, the light conveyer 340 may be removable or may be fixedly attached to the end cap. The inner cavity 126 of the inner connector interface can have an inner shoulder 332, and the light conveyer 340 can rest against the inner shoulder 332 when the light conveyer 340 is in a fully inserted position. The location of the inner shoulder 332 within the inner cavity 126 can determine the fully inserted position.

The light conveyer 340 can convey light rays 350 through the light conveyer and emit the light rays 350 out of the light conveyer. The light rays can be emitted from the light conveyer into and through the inner connector interface 120.

The light rays 350 can pass through the optic 130, and the light rays can pass through the inner connector interface body 220 and out of the outer surface 122. The emitted light rays can pass through the inner connector interface 120, including the optic 130, so that light rays strikes various surfaces on the medical device that can include a catheter and/or a connector.

The light rays can be any predetermined wavelength suitable for the application. By way of non-limiting example, the light rays can be ultraviolet light. By way of further non-limiting example the light rays can be ultraviolet light in the UV-C or UV-B range. By way of further non-limiting example, the light rays can be of a wavelength in the range 255-300 nm. The light rays 350 can be transmitted through the light conveyer 340 with or without internal reflections off the side surfaces 344 and be emitted from the end surface 342. The light rays can be emitted at different angles from the end surface 342 and can be transmitted through the inner connector interface body 120 and/or the optic 130. In various embodiments, the light conveyer 340 can be a light pipe, and the light pipe can transmit light rays with high angles through the physical mechanism of total internal reflection; the light rays can then be emitted from the end surface 342 and pass through the body 120.

FIG. 4 is a partially-cut away view of an optic with a retention feature, according to an illustrative embodiment. Optic 130 can be a lens, window, light pipe, or other optical element. Optic 130 can have an outer surface 212, an inner surface 214, and a circumferential surface 404. Light can pass through the optical element 130, entering the optic through the inner surface 214 and exiting through the outer surface 212. The inner surface 214 and outer surface 212 can be optical interfaces which can refract, reflect, diffract, diffuse or otherwise modify or control the path of light passing through the optical element 130.

Optical element 130 can have one or more retainers 402. Retainers 402 can be, by way of non-limiting example, one or more ridges, holes, grooves, blind holes, or protrusions, or other types of features which can be secured into complementary features on another object such as an inner connector interface body. In various embodiments, the retainer 402 can be a groove around all or a portion of the optic 130, and the inner connector interface body can have a corresponding ridge that can be embedded within the groove. The corresponding ridge of the inner connector interface body can fill the groove and secure the optic.

Optical element 130 can be made from a material such as plastic, glass, fused silica, sapphire, cyclic olefin polymer or copolymer, FEP, ETFE, PMMA, acrylic, or another material suitable for use in a particular application. Optical element 130 can be made from a material suitable for transmitting a predetermined wavelength or wavelengths of light, such as ultraviolet, visible, or infrared light, by way of non-limiting example. By way of further non-limiting example, optical element 130 can be made from UV-grade fused silica and be used to transmit light in the UV-C and UV-B ranges of light, such as approximately 255 nm to 300 nm.

Figure 5:
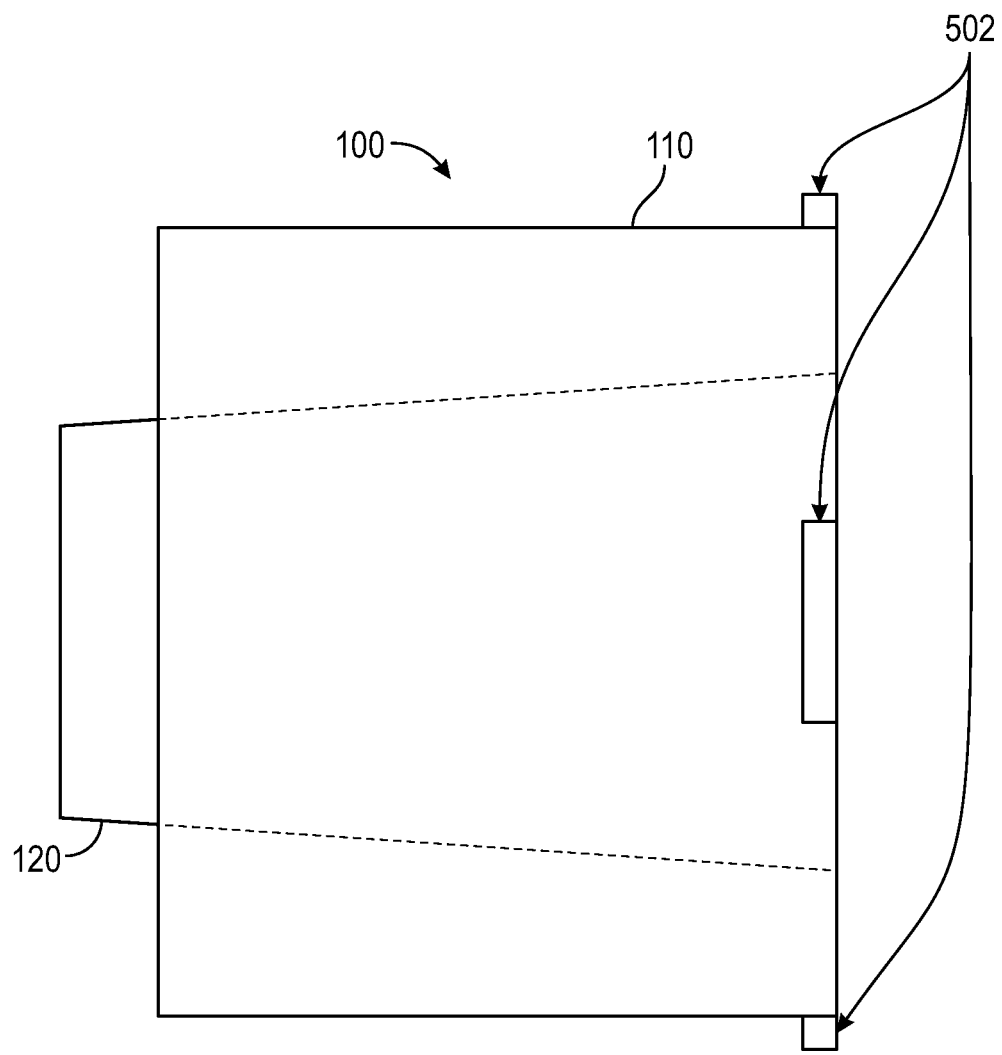
FIG. 5 is a side view of a disinfecting cap with securing points to secure the disinfecting cap to a medical device, according to an illustrative embodiment.

FIG. 5 is a side view of a disinfecting cap with securing points to secure the disinfecting cap to a medical device, according to an illustrative embodiment. The disinfecting cap 100 can have an outer shroud 110, an inner connector interface (shown partly in broken lines), and one or more securing points 502. The securing points 502 can be used to securely connect the cap 100 to a separate object such as a medical device, using complementary receiving features on the separate object. The securing points 502 can allow the disinfecting cap 100 to be selectably connected to and disconnected from the separate object that can be a medical device. By way of non-limiting example, the securing points 502 can be tabs or hooks or other features. The securing points can correspond to various standards for the connection to medical devices, including a Luer standard. In various embodiments, the securing points 502 can be protruding features, and the complementary receiving features on the medical device can be indentations, depressions, or other recessed features. In various embodiments, the securing points 502 can be indentations, depressions, or other recessed features, and the complementary receiving features on the medical device can be protruding features. In various embodiments, the securing points 502 can safely disconnect from the complementary receiving features under certain conditions, such as, by way of non-limiting example, if the connection were subjected to excess tension, or compression, or other force.

Figure 6C:
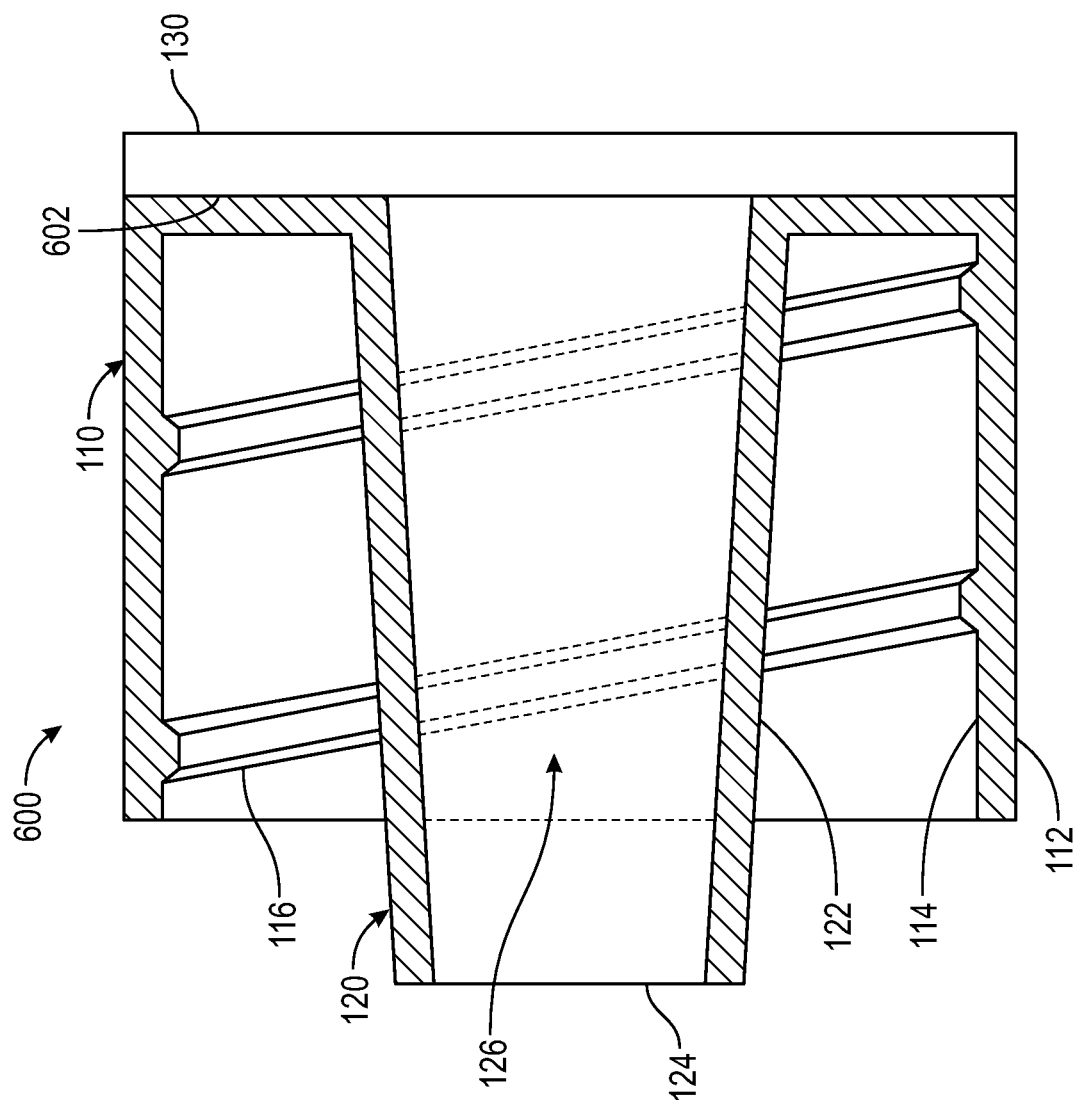
FIG. 6C is a partially-cut away view of a cap and a separate optical element bonded together, showing interior areas, according to an illustrative embodiment.
Figure 6B:
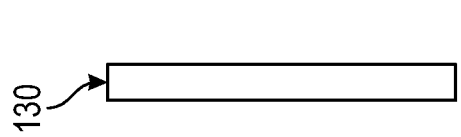
FIG. 6B is a side view of an optic, according to an illustrative embodiment.
Figure 6A:
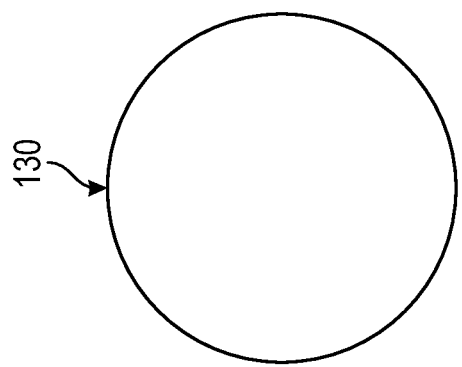
FIG. 6A is a top view of an optic, according to an illustrative embodiment.

FIG. 6A is a top view of an optic, according to an illustrative embodiment, and FIG. 6B is a side view of an optic, according to an illustrative embodiment. The optic 130 can be a flat disc window. The optic 130 can be made from various materials, including TOPAS COC 8007X10. A 2-millimeter-thick optic made from TOPAS COC 8007X10 can have about 35% transmission at 260 nm, a one-millimeter thick optic can have about 59% transmission, a ⅔-millimeter-thick optic can have about 70.47% transmission, and a ¾ mm thick optic can have about 67.46% transmission at 260 nm.

A thinner optic can be desirable for increased transmission, while the disinfecting cap, including the outer shroud and the inner connector interface, can benefit from having an increased wall thickness that can result in increased structural strength. However, having variable wall thickness can increase the difficulty of injection molding, so it can be desirable to separately mold a thinner optic and thicker structural portions of the cap. Structural portions of the cap can include the inner connector interface and the outer shroud. After the structural portions and the optic have been molded separately, they can be assembled together using a physical or chemical adhesive, a laser welding operation, an ultrasonic welding operation, or some other operation to attach the optic to the body of the disinfecting cap. The cap can have various bonding seams that can be exposed for thermal bonding. The bonding seam can be heated directly so as not to deform the other parts of the cap. The bonding seam can be designed to be outside the optical path and therefore not interfere with the transmission of light through the optical path (i.e., the optical characteristics of the bonded seam or joint would not alter the path of light passing through the optical path of the end cap via refraction, reflection, diffraction, etc.).

FIG. 6C is a partially-cut away view of a cap and a separate optic bonded together, showing interior areas, according to an illustrative embodiment. A disinfecting cap 600 can have two or more non-unitary, separate components, that can include an optic 130, and structural portions of a disinfecting cap including an outer shroud 110 and inner connector interface 120. The optic 30 can be on the outside of the cap 600, and can have a common exposed edge with the end cap 600. The common exposed edge of the optic and the rest of the end cap can then be heated in a targeted (i.e., localized) way so that parts of the optic and the end cap melt and become molten and fuse together. The molten edge can be cooled passively or by actively removing heat, so that it solidifies and the two individual pieces are fused together at a seam 602.

The end cap body, including the inner connector interface 120 and the outer shroud 110, and the optical element 130 can be joined at the seam 602 using various chemical or physical adhesives, ultrasonic welding, thermal bonding, or various other bonding. The optic 130 and the end cap body can be made separately but from the same type of base material. By way of non-limiting example, the base material can be a plastic such as cyclic olefin polymer (COP) or cyclic olefin copolymer (COC). If the optic 130 and the end cap body are made from the same type of base material, they can be fused together using a thermal bonding technique. The seam 602 at the junction of the optic 130 and the end cap body can be heated in a targeted way so that some parts of the optic 130 and the end cap body melt, and become molten, and fuse together, while other parts are not affected by the heat. Then, the seam 602 can be cooled passively or by actively removing heat, so that it solidifies. This thermal fusing technique or method can also be used if the optic 130 is positioned inside the end cap as in FIGS. 6D and 6E.

Figure 6E:
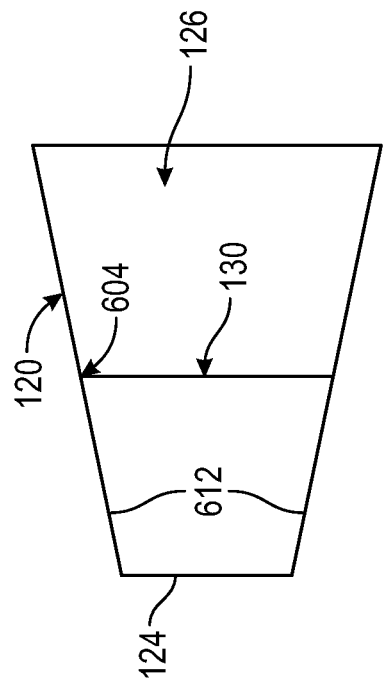
FIG. 6E is a cross section view of the optic within an inner connector interface of FIG. 6D, taken along cross section lines 6E-6E of FIG. 6D, according to the illustrative embodiment.
Figure 6D:
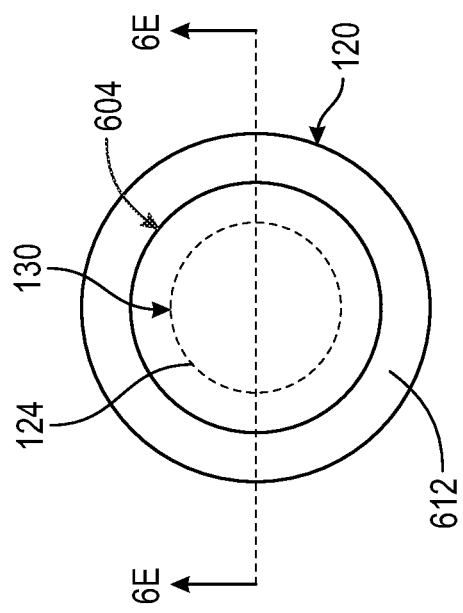
FIG. 6D an end view from the rear of the end cap, showing an optic within an inner connector interface an bonded to the inner surface of the inner connector interface, according to an illustrative embodiment.

FIG. 6D is an end view from the rear of the end cap, showing an optic within an inner connector interface an bonded to the inner surface of the inner connector interface, according to an illustrative embodiment, and FIG. 6E is a cross section view of the optic within an inner connector interface of FIG. 6D, taken along cross section lines 6E-6E of FIG. 6D, according to the illustrative embodiment. The optic 130 can be bonded within the inner connector interface 120 of the end cap body at a seam 604 between the inner sidewall 612 of the inner connector interface 120 and the optic 130.

It is specifically contemplated that the joint or joints between the separate optic and the end cap body can be at any arbitrary location within the end cap or outside of the end cap as long as the joint is constructed in such a way as to meet the mechanical bonding strength requirements, or fluid- or air-sealing requirements, or optical requirements, or any combination of the above requirements for the specific application for which the end cap and optic is intended.

Figure 7A:
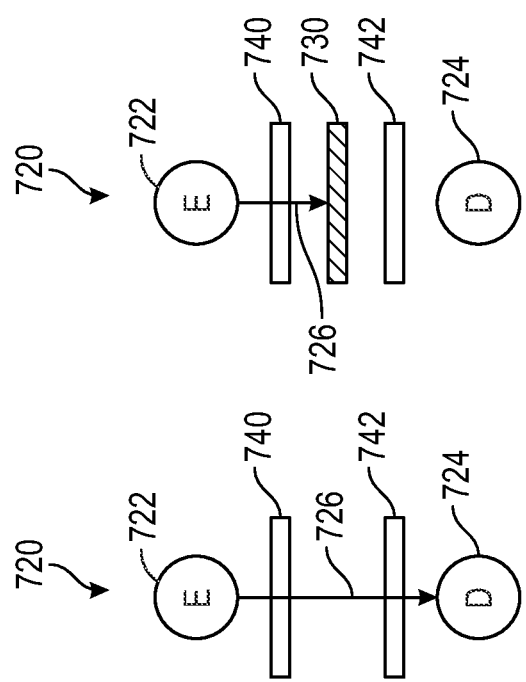
FIG. 7A is a schematic diagram of an external light source with a photointerruptor sensing system, according to an illustrative embodiment.

FIG. 7A is a schematic diagram of an external light source with a photointerruptor sensing system, according to an illustrative embodiment. In various embodiments, an external light source 700 can be used in conjunction with the end cap. The end cap and the external light source can include features that can work together to detect if the end cap is securely connected to the connector port of the medical device and if the end cap is connected securely to the external light source. By way of non-limiting example, an external light source 700 can include a primary UV germicidal light emitter 710 and a photointerruptor system 720. The primary light emitter 710 can emit light that can travel outside of the external light source, through the disinfecting end cap 712, and into the medical device 714 to sterilize the medical device.

The photointerruptor system 720 of the auxillary light source can include an auxiliary light emitter 722 and a photo sensor 724. The auxiliary light emitter 722 can emit a different wavelength than the primary UV germicidal light emitter 710, or it can emit the same wavelength. By way of non-limiting example, the auxiliary light emitter 722 can be an infrared light emitter in the wavelength range 700-1,000,000 nm, or it can be a visible light emitter in the range 400-700 nm, or it can be an ultraviolet light emitter in the range 100-400 nm. By way of non-limiting example, the auxillary emitter 722 can be an LED and the photosensor 724 can be a photodiode. The light from the auxillary light emitter 722 can follow an optical path 726 between the auxillary light emitter 722 and the photosensor 724 that can be interrupted only when the end cap is securely connected to both the external light source and to the target medical device. The external light source 700 can include a system controller 728 that can be operatively connected to the photointerruptor system 720 and can be operatively connected to the primary light emitter 710. The system controller 728 can detect the interruption, and the system controller 728 can use this information as a signal to prevent or allow the primary germicidal light emitter 710 to be turned on. This can be a safety feature if, by way of non-limiting example, the primary germicidal light emitter 710 can emit wavelengths that can have potentially harmful effects on human tissue.

Figure 7B:
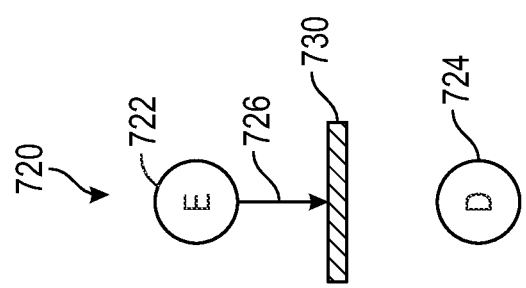
FIG. 7B is a schematic diagram of a photointerruptor sensing system with a light blocker, according to an illustrative embodiment.

FIG. 7B is a schematic diagram of a photointerruptor sensing system with a light blocker, according to an illustrative embodiment. An end cap or end cap assembly can have a light blocker 730 which can change optical transmission properties of an internal or external optical path 726. By way of non-limiting example, light blocker 730 can block the light, however, in various embodiments the light blocker 730 can also reduce the transmittivity, or increase absorption, or increase attenuation, or increase reflectivity of the optical path 726. The light blocking can be activated or deactivated, or can be changed or adjusted gradually over a continuous range. A light blocker 730 can be controlled depending on whether the end cap is connected to a medical device or a disinfecting UV light emitter or both.

An end cap or can have a mechanical linkage which can change the profile of the end cap. By way of non-limiting example, the mechanical linkage can include a light blocker such as a peg, a shaft, a column, or another such feature which can be raised up and can protrude out from the outer surface of the end cap. The mechanical linkage can cause the light blocker to be raised out from the surface of the end cap when the end cap is connected to an auxiliary light source, or a medical device, or both. The light blocker can be activated or deactivated, or can be changed or adjusted gradually over a continuous range. The activation or deactivation, or gradual adjustment, of the light blocker can be controlled by the connection state of the end cap in relation to the external light source or medical device. By way of non-limiting example, the light blocker can be activated if the end cap were connected to an external light source. By way of further non-limiting example, the light blocker can be activated if the end cap were connected to an external light source and a medical device. By way of further non-limiting example, the light blocker can be deactivated if the end cap is connected to an external light source and can be activated if the end cap is not connected to the external light source.

Turning to FIGS. 7A and 7B, the light blocker 730 of the end cap which can change the optical transmission properties of the internal or external optical path 726 can work in conjunction with the external light source 700 to detect the connection state of the end cap in relation to the external light source and/or medical device. By way of non-limiting example, an external light source 700 can have an auxiliary light emitter 722 and a photosensor 724 with an optical path 726 between them. A light blocker 730 of the end cap can interfere with the optical path 726. In a first, unblocked state, as shown in FIG. 7A, the end cap is not fully in the disinfecting position, and the light blocker is not blocking the optical path. In the second, blocked state, as shown in FIG. 7B, the end cap is connected to the medical device, resulting in the light blocker 730 blocking the optical path 726. The photointerruptor system 720 can detect whether or not the end cap is connected to the medical device based upon the strength of the signal received by the photosensor 724. In this way the light blocker of the end cap that can change the optical transmission properties of an optical path of the photointerruptor system to trigger the photointerruptor system and indicate that the end cap is connected to the medical device. In various embodiments, an end cap can consist of an end cap body, a light transmitter, and a mechanical linkage that can be spring loaded, explained more fully below.

Figure 7C:
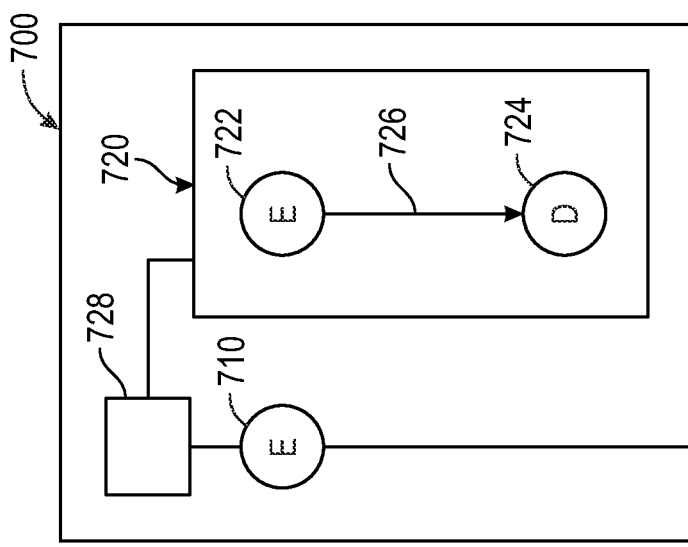
FIG. 7C is a schematic diagram of a photointerruptor sensing system with light transmitters, according to an illustrative embodiment.
Figure 7D:
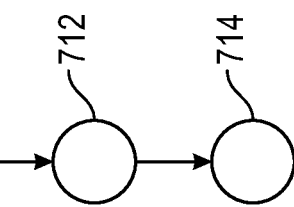
FIG. 7D is a schematic diagram of a photointerruptor sensing system with light transmitters and a light blocker, according to an illustrative embodiment.

FIG. 7C is a schematic diagram of a photointerruptor sensing system with light transmitters, according to an illustrative embodiment. The photointerruptor system can include a light emitter 722 a light detector 724, and one or more light transmitters 740 and 742. Light transmitters 740 and 742 can be part of an end cap. FIG. 7D is a schematic diagram of a photointerruptor sensing system with light transmitters and a light blocker, according to an illustrative embodiment. The light blocker 730 can block the optical path 726, thereby indicating that the end cap is in place. The photointerruptor system 720 can detect the presence or absence of a light blocker 730 between the emitter 722 and the photosensor 724, and the photointerruptor system 720 can output a signal allowing the primary light emitter to be illuminated when the light blocker 730 blocks the optical path 726. The signal can be detected by a system controller 728, which can be, by way of non-limiting example, a microcontroller or other electronic system. The system controller 728 can control the primary light emitter 710, and can use the signal from the photointerruptor system 720 to determine whether the primary light emitter 710 can be switched on. In various embodiments, the light transmitters 740 and 742 can be designed so that they are not detected by the photointerruptor system 720, and the photointerruptor detects only the presence of the light blocker. In various embodiments, the light transmitters can be detected by the photointerruptor system, thereby indicating that the end cap is securely connected to the external light source 700.

Figure 7F:
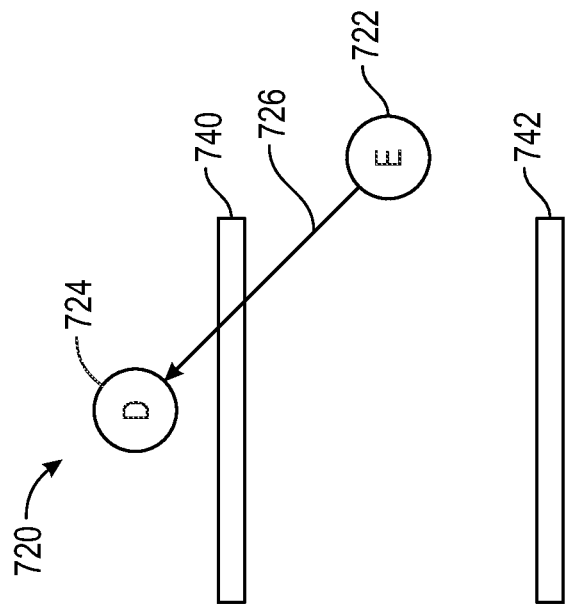
FIG. 7F is a schematic diagram of the photodetector system of FIG. 7E with the cap removed and the light striking the photodetector, according to an illustrative embodiment.
Figure 7E:
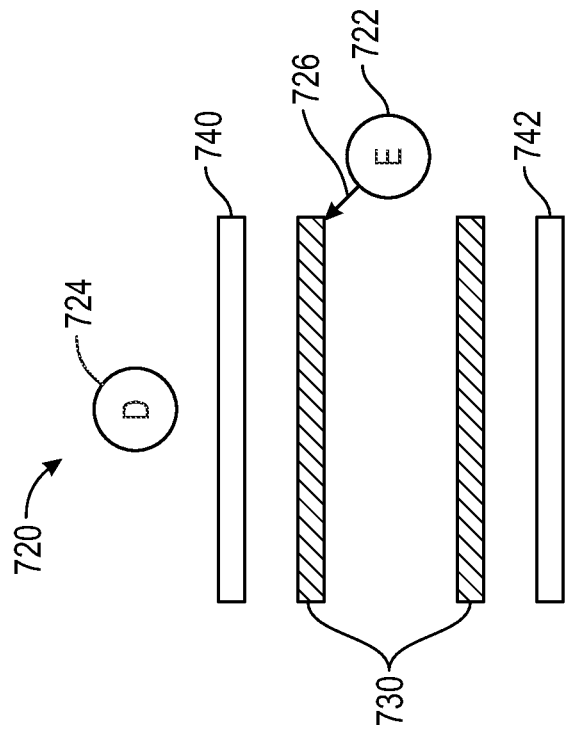
FIG. 7E is a schematic diagram of a photodetector system with a light source at a rear of a cap, and a photosensor at a side of the cap, according to an illustrative embodiment.

FIG. 7E is a schematic diagram of is a schematic diagram of a photodetector system with a light source at a rear of a cap, and a photosensor at a side of the cap, according to an illustrative embodiment. As explained more fully below in connection with FIG. 8C, a light emitter 722 can be positioned at the rear of a cap, and one or more photodetectors 724 can be positioned to the side of a cap. In various embodiments, the cap can function as a light blocker 730, or the cap can include a separate light blocking component that can be the light blocker 730.

FIG. 7F is a schematic diagram of the photodetector system of FIG. 7E with the cap removed and the light striking the photodetector, according to an illustrative embodiment. As shown in FIG. 7F, when the cap is not present in the system, light from the light emitter 722 can strike the photosensor 724. When light from the light emitter 722 strikes the photosensor 724, the system can be prevented from using the high-intensity sterilizing light, explained more fully below in connection with FIG. 8C.

The light emitted from the auxiliary emitter 722 can be continuous, or pulsed, or otherwise time-varying to allow more sophisticated sensing algorithms to reject ambient light and "lock-in" on only the light emitted by the auxiliary light emitter 722. In this way the photointerruptor system 720 and the system controller 728 can be made insensitive to interference from environmental or ambient light.

Figure 8A:
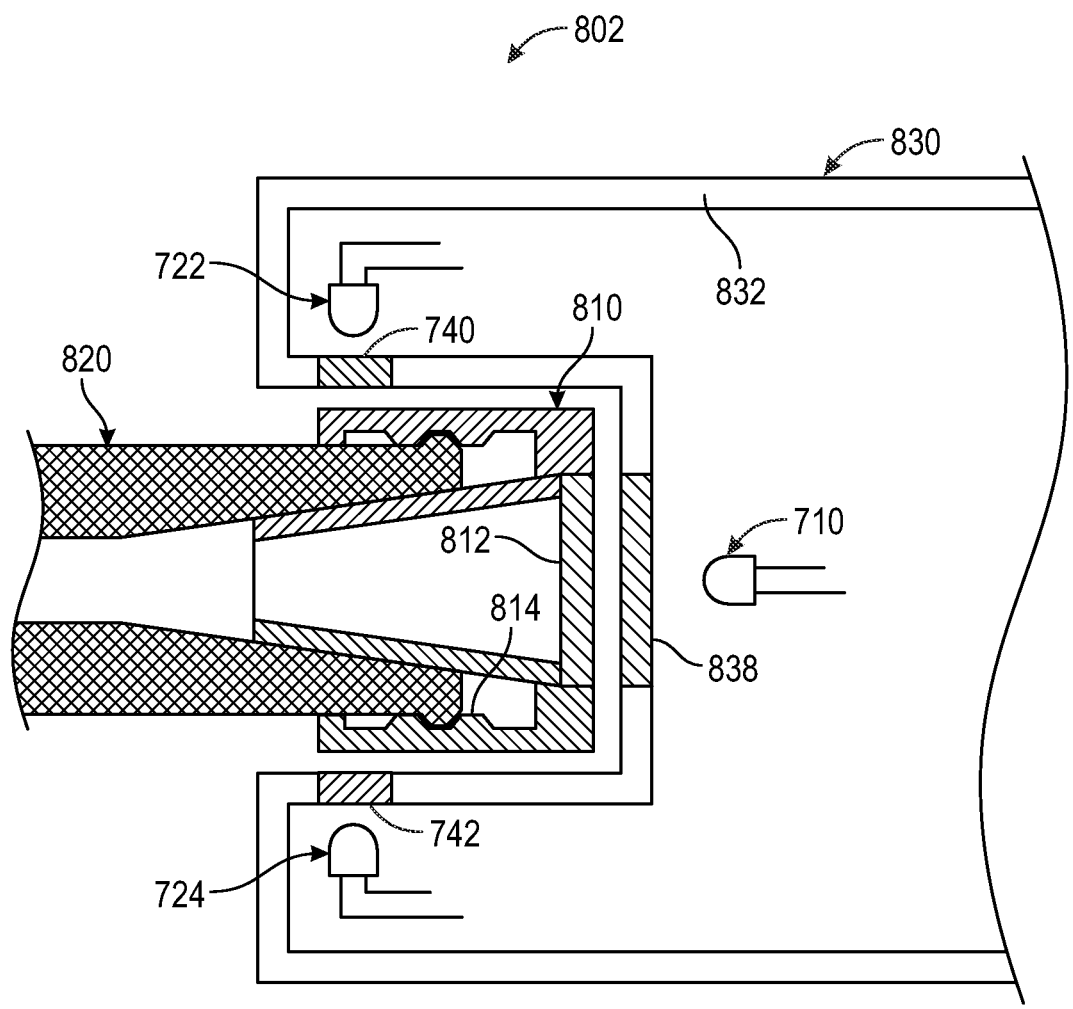
FIG. 8A is a partially cut away view of a sterilization system showing the inner workings, with an end cap attached to an external light source and a medical device, according to an exemplary embodiment.

FIG. 8A is a partially cut away view of a sterilization system showing the inner workings, with an end cap attached to an external light source and a medical device, according to an exemplary embodiment. The sterilization system 802 can have an end cap 810 and an external light source 830. The end cap 810 of the sterilization system 802 can be connected to a connector 820 of a separate object, such as a medical device, which can be disinfected or sterilized by the system 802. By way of non-limiting example, the connector 820 can be a catheter hub having a female Luer fitting conforming to a standard such as ISO 594, or another standard, or a proprietary design. The external light source 830 can have an outer enclosure 832, one or more primary disinfecting light emitters 710, one or more auxiliary light emitters 722, one or more light transmitters 740, 742, one or more photosensors 724, and one or more disinfecting light passageway 838.

The end cap 810 can have a connector interface to complement the connector 820 of the separate object, such as a medical device, that is to be disinfected. The end cap 810 can have internal threading 814 to securely attach to complementary threading on the connector 820. By way of non-limiting example, the end cap connector interface and threading 814 can conform to a standard such as ISO 594, another standard, or a proprietary design.

The end cap 810 can have an optic 812. The optic can be a window, or a lens, or a lens array, or a light pipe, or a light homogenizer, another type of optic. The end cap 810 and optic 812 can be made from optical materials suitable for transmitting or blocking certain wavelengths or ranges of wavelengths as desired. By way of non-limiting example, the end cap 810 and optic 812 can be made from a plastic such as cyclic olefin polymer (COP) or copolymer (COC), FEP, ETFE, PMMA or another plastic. By way of further non-limiting example, the end cap 810 and optic 812 can be made from glass, or fused silica, or sapphire, or another material. The end cap 810 and optic 812 can be made from the same material or different materials. The optic 812 can be an integrated component of the end cap 810, or it can be a separate component manufactured separately from the end cap 810 and then attached to the end cap. The end cap 810 and optic 812 can be made using manufacturing techniques such as injection molding, thermoforming, cutting, milling, grinding, 3D printing, or another manufacturing technique or a combination of techniques. The end cap 810 and optic 812 can be made using the same manufacturing technique or combination thereof, or a different technique or combination thereof.

In the embodiment shown in FIG. 8A, the connector 820 can function as a light blocker by blocking the optical path between the auxiliary light emitter 722 and the photosensor 724. When the connector 820 is not connected in the system, there can be a clear optical path from one or more auxiliary light emitters 722 to one or more photosensors 724; when the connector 820 is connected, the optical path is blocked or interrupted. The one or more photosensors 724 can output a digital or analog signal based on the state of the optical path, and a system controller unit can receive the signal and use it to change the functionality of the system based on the state of the signal. By way of non-limiting example, the system controller can be a microcontroller, or microprocessor, or other type of digital electronic system. By way of further non-limiting example, the system controller can change the functionality of the system to prevent the user from turning on the disinfecting light source when the optical path is unblocked.

The one or more primary disinfecting light emitters 710 can emit light at one or more wavelengths or ranges of wavelengths. One or more primary disinfecting light emitters 710 can emit disinfecting light through one or more disinfecting light passageways 838 into an end cap 810 through optic 812. By way of non-limiting example, the one or more primary disinfecting light emitters 710 can be LEDs, xenon arc lamps, mercury lamps, lasers, laser diodes, or other types of light sources. By way of non-limiting example, the one or more disinfecting light passageways 838 can be windows, lenses, lens arrays, light pipes, light homogenizers, or other types of optical components or a combination of different optical components. The disinfecting light can pass through the end cap 810 and into the connector 820 and other parts of the separate object or device to be sterilized.

The one or more auxiliary light emitters 722 can emit light at one or more wavelengths or ranges of wavelengths. The light from the one or more auxiliary light emitters 722 can pass through the one or more emitter light transmitters 740 and can travel through an optical path, which can include one or more detector light transmitters 742, terminating at one or more photosensors 724. The one or more photosensors can receive and be sensitive to one or more wavelengths or ranges of wavelengths. By way of non-limiting example, the one or more auxiliary light emitters 722 can be LEDs, incandescent bulbs, arc lamps, lasers, or other types of emitters. By way of non-limiting example, the one or more photosensors 724 can be photodiodes, phototransistors, or other types of photodetectors.

Figure 8B:
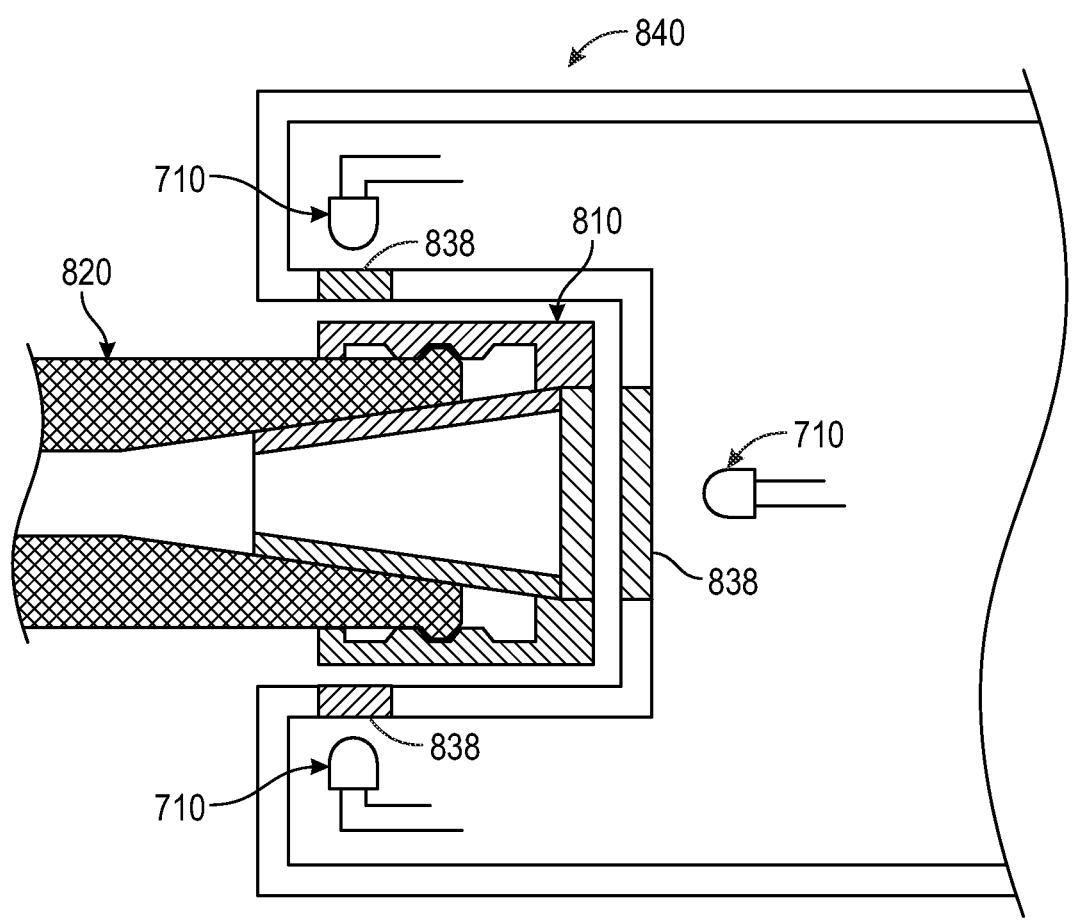
FIG. 8B is a partially cut-away view of a sterilization system showing the inner workings, with multiple disinfecting light sources emitting light from different locations and at different angles, according to an illustrative embodiment.

FIG. 8B is a partially cut-away view of a sterilization system showing the inner workings, with multiple disinfecting light sources emitting light from different locations and at different angles, according to an illustrative embodiment. The sterilization system 840 can have three primary disinfecting light emitters 710 and three disinfecting light passageways 838; and the primary disinfecting light emitters 710 and disinfecting light passageways 838 can surround the end cap 810 and connector 820. The primary disinfecting light emitters 710 can emit disinfecting light onto the end cap 810 and connector 820 from multiple angles and directions. The disinfecting light can be transmitted through the end cap 810 to disinfect the outside surfaces of the connector 820.

Figure 8C:
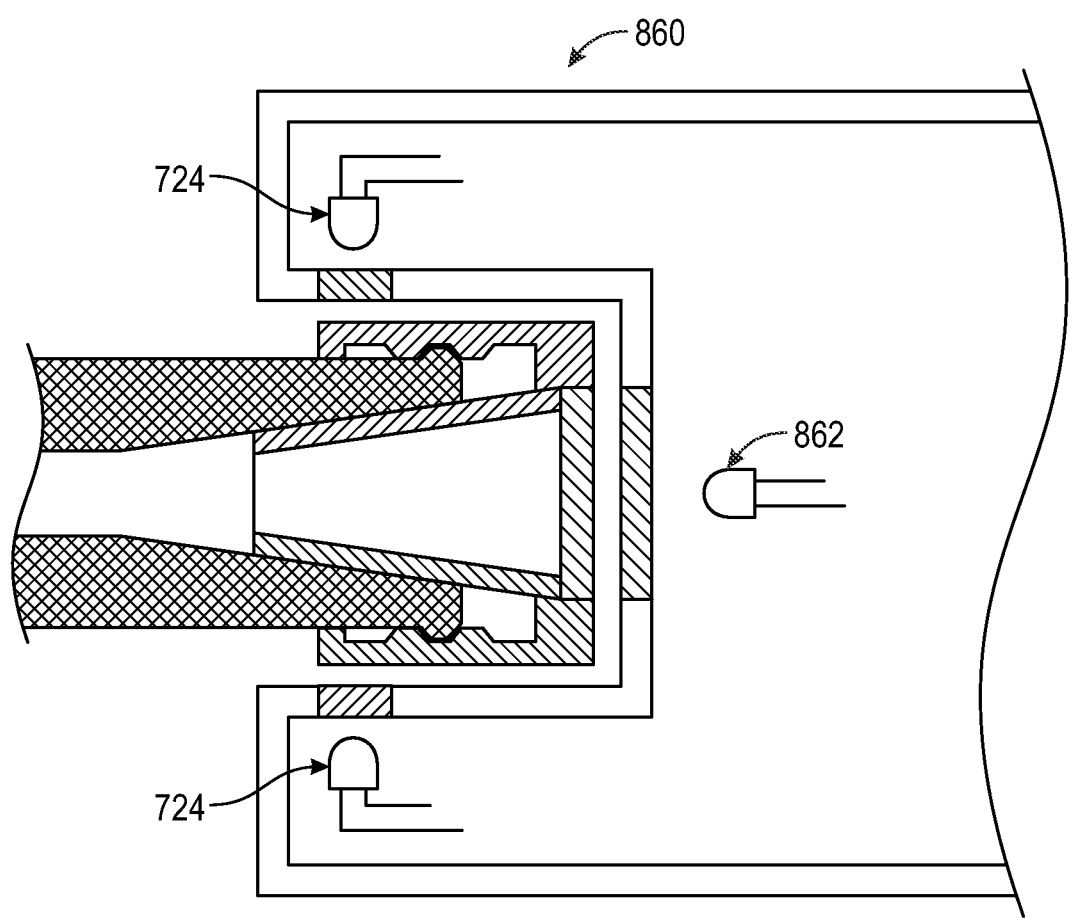
FIG. 8C is a partially cut-away view of a sterilization system showing the inner workings, with a light emitter that functions as a primary disinfecting light emitter and an auxiliary light emitter, according to an illustrative embodiment.

FIG. 8C is a partially cut-away view of a sterilization system showing the inner workings, with a light emitter that functions as a primary disinfecting light emitter and an auxiliary light emitter, according to an illustrative embodiment. FIG. 8C is an embodiment of the disinfection or sterilization system 860 with a combination light emitter 862 that can be both a primary disinfecting light emitter and an auxiliary emitter. The sterilization system 860 can have one or more photosensors 724 that can detect light from the combination light emitter. In various embodiments, the combination light emitter 862 can emit a first light at a first light intensity that can be a reduced intensity, and if the photosensor(s) 724 do not detect the first light, the combination light emitter can increase the light intensity to a second light at a second light intensity. In various embodiments, the combination light emitter 862 can begin with light at a full intensity, and if the photosensor 724 detects the light from the light emitter above a predetermined threshold of light intensity, the system can switch power to the light emitter 862 off, and can provide an error message. In various embodiments, the system can lock out for a predetermined period of time after the photosensor 724 detects light form the light emitter above a predetermined threshold.

Figure 9A:
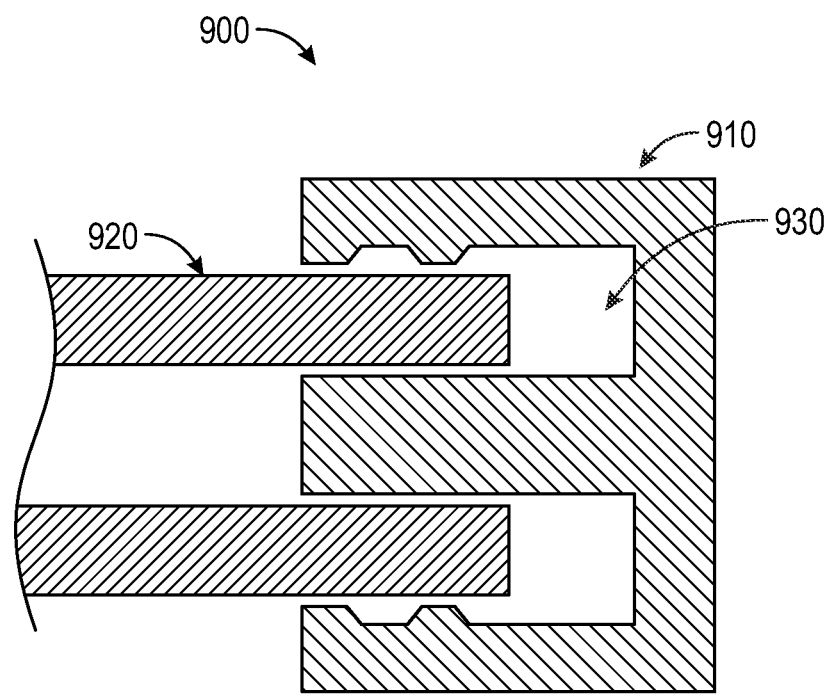
FIG. 9A is a partially cut-away view of a connector system showing the inner workings, according to an illustrative embodiment.

FIG. 9A is a partially cut-away view of a connector system showing the inner workings, according to an illustrative embodiment. A connector system 900 can include an end cap 910 and the connector 920 of a connected device such as, for example, a medical device. The end cap 910 can include, by way of non-limiting example, a male Luer lock, or other components that conform to at least a portion of a male Luer lock standard with internal threads. At least a portion of the connector 920 can enter an engagement region 930 of the end cap 910. The at least a portion of the connector 920 can enter engagement region 930 when the connector 920 is connected to the end cap 910 and can leave the engagement region 930 when connector 920 is disconnected from the end cap 910.

Figure 9C:
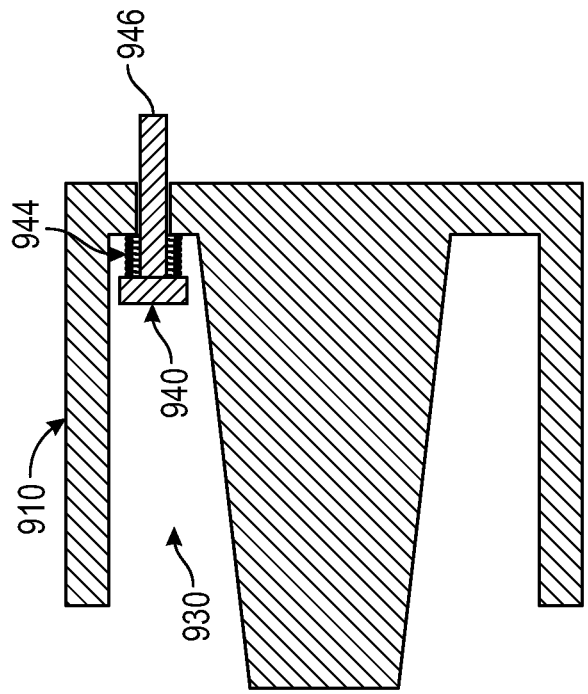
FIG. 9C is a partially cut-away view of a connector system showing the inner workings with a mechanical linkage in a connected conformation, according to an illustrative embodiment.
Figure 9B:
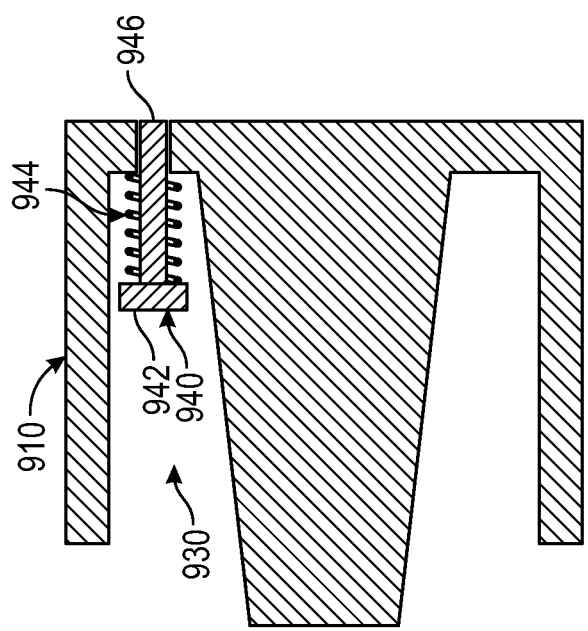
FIG. 9B is a partially cut-away view of a connector system showing the inner workings with a mechanical linkage, according to an illustrative embodiment.

FIG. 9B is a partially cut-away view of a connector system showing the inner workings with a mechanical linkage, according to an illustrative embodiment. In various embodiments, the mechanical linkage can be a switch. The mechanical linkage can be held captive within the end cap so that it can be free to move but cannot fall out or become separated from the end cap. The end cap 910 can have a mechanical linkage 940 that can change position in response to the presence of a connector 920. A mechanical linkage 940 can include an actuator 942, a spring 944, and a throw 946.

FIG. 9C is a partially cut-away view of a connector system showing the inner workings with a mechanical linkage in a connected conformation, according to an illustrative embodiment. Turning to FIGS. 9A and 9C, a connector 920 can actuate the actuator 942 when it enters engagement region 930, and the throw 946 can change location via spring 920 in response to the actuation. In various embodiments, the throw 946 can change the optical transmission properties of an optical path. In various embodiments, the throw 946 can change the internal or external mechanical profile of the end cap. Although the connector 920 has been omitted from FIG. 9C for the sake of clarity, it should be clear that the connector can cause the change in location of the throw 946 from the first location shown in FIG. 9B to the second location shown in FIG. 9C.

Figure 10:
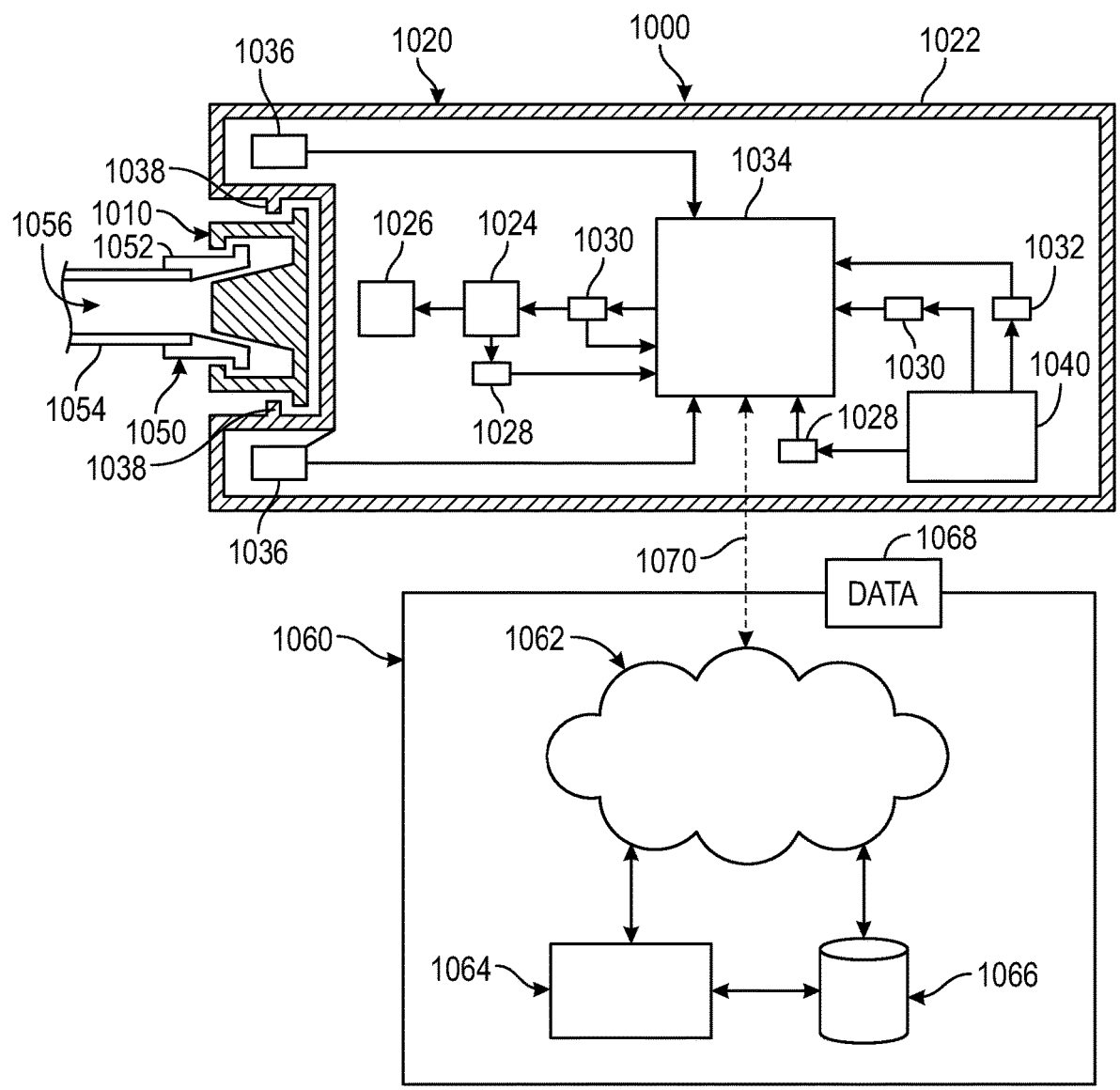
FIG. 10 is a partially-cut away view of a disinfection system with a remote monitoring system for data collection, communication and control, showing a schematic diagram of the inner workings, according to an illustrative embodiment.

FIG. 10 is a partially-cut away view of a disinfection system with a remote monitoring system for data collection, communication and control, showing a schematic diagram of the inner workings, according to an illustrative embodiment. A sterilization system 1000 can include an end cap 1010, a sterilizer 1020, a medical device 1050 that can undergo sterilization, and a remote monitoring system 1060 for data collection, communication and control.

A sterilizer 1020 can be an external light source, as described above. A sterilizer 1020 can have a housing 1022 which houses the internal components. Sterilizer 1020 can have a primary disinfecting light emitter 1024, a disinfecting light passageway 1026, one or more temperature monitors (thermometers) 1028, one or more current monitors (ammeters) 1030, one or more voltage monitors (voltmeters) 1032, a light source controller 1034, one or more radiant power monitors 1036, attachment features 1038 for securing an end cap, or any combination of the above. The sterilizer can have a power source 1040 that can be an internal power source such as a battery, or can provide power from an external source such as an external battery or other electrical connection.

A medical device 1050 can be a catheter system. The medical device 1050 can have a female coupling 1052, such as a female Luer fitting, and a catheter tube 1054 with a catheter lumen 1056. Disinfecting light can be emitted by the sterilizer 1020, and can pass through the end cap 1010 to the female coupling 1052 and the catheter tube 1054. The disinfecting light can illuminate the inner surfaces of the female coupling 1052 and the catheter lumen 1056.

Remote monitoring system 1060 can have a communication network 1062, a processor 1064, and a database (db)

1066. A data connection 1070 can share data 1068 from the sterilizer 1020 with the remote monitoring system 1060. Data 1068 can be shared unidirectionally or bidirectionally between the light source controller 1034 and the remote monitoring system 1040. Data 1068 can include system status information gathered from the sterilizer about the status and performance of the sterilizer. The remote monitoring system 1040 can maintain the status of the sterilizer, and can maintain a record of the system status information. System status information can be measured by sensors (by way of non-limiting example, temperature monitors 1028, current monitors 1030, voltage monitors 1032, radiant power monitors 1036, etc.) and can be received by light source controller 1034. The light source controller 1034 can share the data with the remote monitoring system. The light source controller 1034 can also monitor the incoming data, and can identify potential problems such as degraded or nonideal operating conditions including decreased light source intensity due to wear and aging, ambient temperature, or depleted electrical power reserves. The light source controller 1034 can then implement a self-healing solution by adjusting the light source intensity, duration of exposure, or both based upon the sensor measurements to compensate for degraded or non-ideal operating conditions.

The remote monitoring system can monitor the health and welfare of the device. The monitoring can include how many hours a light source has been used, how often the light source has been used, how many times the battery has been recharged, how many times the battery has been completely discharged, how many times the battery was completely charged, etc. The remote monitoring system can monitor use of the device and can inform the user how often the device is used per day, per week, overall, etc. The remote monitoring system can monitor use of the device and can inform the user when the device needs maintenance. The remote monitoring system can inform the user when a particular unit is reporting any performance issues. The remote monitoring system can report compliance issues. Compliance issues can include whether the devices are being used correctly and/or whether the devices are being used for the full time period. The remote monitoring system can monitor the input voltage and/or current being used by the device, and/or can monitor the light intensity, because lower voltage or current can limit the total light energy being delivered by the device. The remote monitoring system can inform the user whether or not the devices have sufficient voltage or current, and/or whether or not the devices are delivering sufficient energy.

Figure 11A:
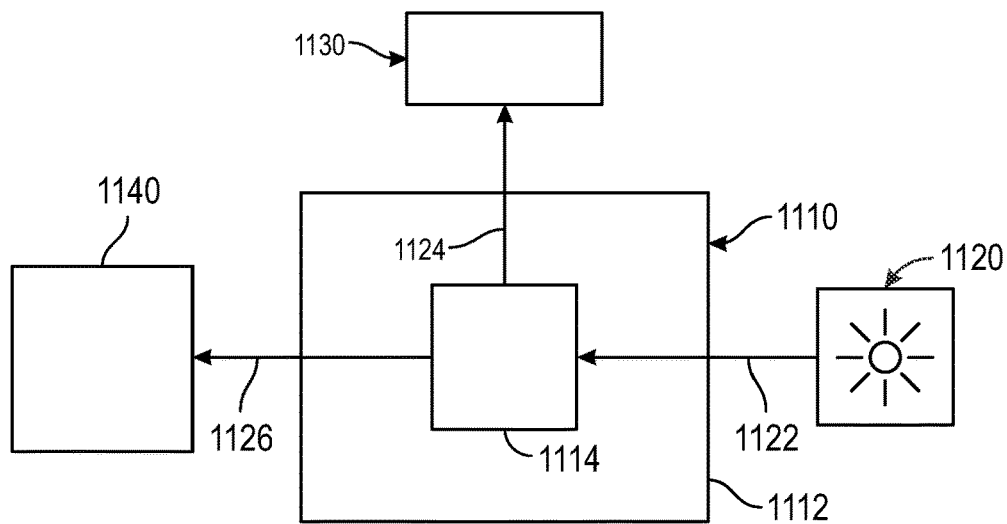
FIG. 11A is a schematic diagram of an end cap with a beam splitter, according to an illustrative embodiment.

FIG. 11A is a schematic diagram of an end cap with a beam splitter, according to an illustrative embodiment. An end cap 1100 can have an end cap body 1112 and one or more beam splitters 1114. By way of non-limiting example, the beam splitters can work by optical refraction or reflection or other means, and can be beam splitters, beam samplers, lenses, lens arrays, or other optics. One or more light sources 1120 can emit light 1122 which can be incident upon, and pass through, an end cap 1110. One or more beam splitters 1114 can be embedded within the end cap 1110 and can redirect all or a portion of the incident light 1122. Light from a light source 1120 can be incident on a beam splitter 1114, and can be split into a redirected portion 1124 and an unredirected, or transmitted portion 1126. The incident light can be part of a main disinfecting light beam and the redirected portion of the light beam can be used for a measurement of overall light energy delivered to the target or for other purposes. The unredirected, or transmitted, part 1126 of incident light 1122 can be transmitted by the end cap to a target 1140 to sterilize the target. Target 1140 can be a medical device such as a catheter. The redirected part 1124 of incident light 1122 can be transmitted by the end cap to one or more sensors 1130. One or more sensors 1130 can receive redirected light 1124 and can transmit information about the light characteristics to other devices or components via electrical signals. By way of non-limiting example, one or more sensors 1130 can be photodiodes, phototransistors, spectrometers, optical power meters, or other types of light sensors. The sensor 1130 can output information about the received light in an output signal. The information can comprise light intensity, radiant power, radiant flux, wavelength, spectral flux, spectral power, polarization state, or other characteristics of the received light. The output signal can be received by a controller or processor, and the controller or processor can be programmed to adjust various functions depending upon the information contained within the received signal. Adjusting various functions can include increasing or decreasing the voltage or current to the LED. Adjusting various functions can include increasing or decreasing the time that the LED is active.

The light 1122 emitted by the one or more light sources can be a single wavelength, or multiple wavelengths, or a continuous spectrum of wavelengths, or multiple continuous spectra of wavelengths, or any combination thereof. By way of non-limiting example, the light can be in the range 250-400 nm. By way of further non-limiting example, the light 1122 can be in the wavelength range 250-280 nm. By way of further non-limiting example, the light can be 265 nm. By way of further non-limiting example, the light can be 280 nm. The light can be polarized or unpolarized.

Figure 11B:
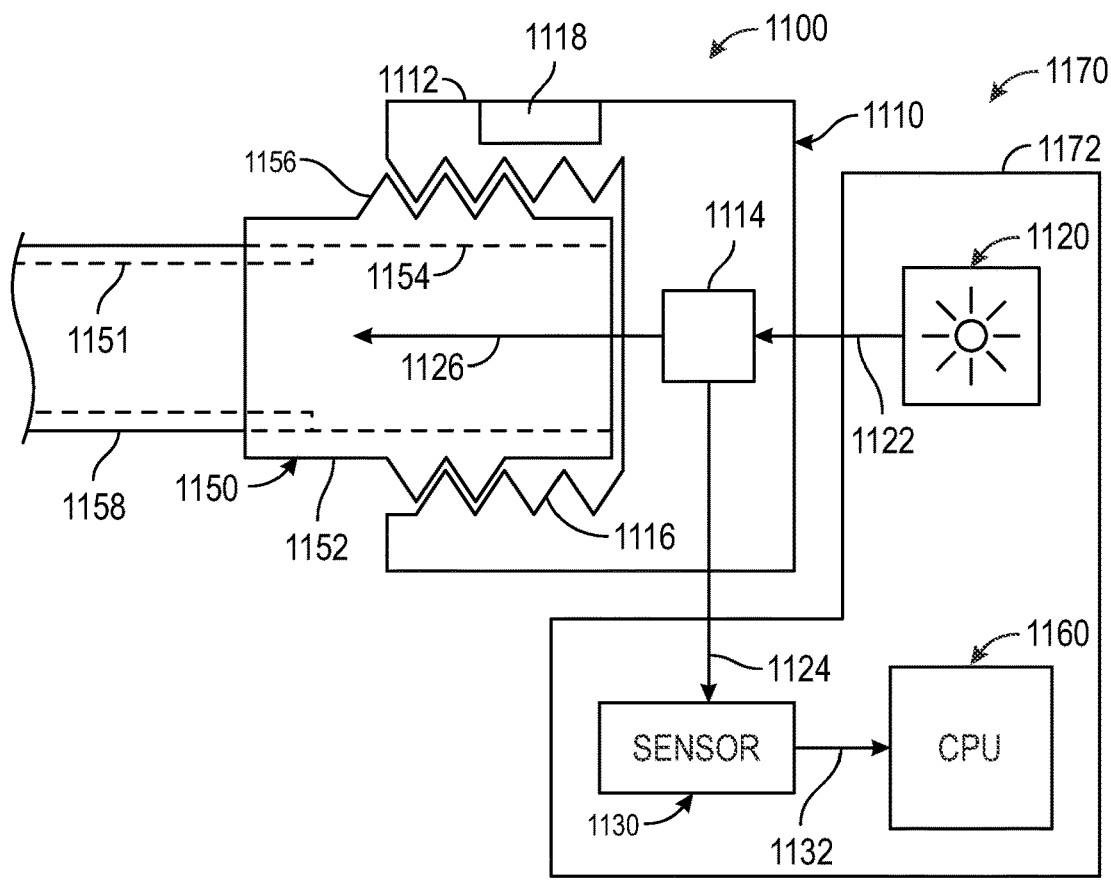
FIG. 11B is a schematic diagram of sterilizer system with an end cap having a beam splitter and an external light source, according to an illustrative embodiment.

FIG. 11B is a schematic diagram of sterilizer system with an end cap having a beam splitter and an external light source, according to an illustrative embodiment. Sterilizer system 1100 can include one or more light sources 1120 that can emit light 1122. The emitted light can be incident upon an end cap 1110 and can travel through the body 1112 of the end cap. The cap can include one or more beam splitters 1114 that can redirect all or part of incident light 1122. The unredirected, or transmitted, part 1126 of incident light 1122 can be transmitted by end cap 1110 to a target 1150. By way of non-limiting example, target 1150 can be a medical device such as a catheter. Target 1150 can have a connector 1152 and a main body 1158. By way of non-limiting example, connector 1152 can be a Luer lock connector and can be compliant with a connector standard such as ISO 594, or another standard, or be compliant with a proprietary design. By way of further non-limiting example, connector 1152 can be a female Luer lock connector. Connector 1152 can have secure attachment features 1156 which can attach to corresponding attachment features 1116 of end cap 1110. By way of non-limiting example, secure attachment features 1156 and 1116 can be screw threads, and by way of further non-limiting example can be ISO 594-compliant screw threads. Target device can have internal connector walls 1154 and internal main body walls 1151. Transmitted light 1126 can irradiate all or part of target device 1150, including inner walls 1151 and 1154. Walls of target device 1151 can be opaque to the light 1126 so that no light or only a very small fraction of the light is transmitted through the walls out of the device.

Redirected light 1124 can be transmitted by end cap 1110 to one or more sensors 1130. Sensors 1130 can receive redirected light 1124 and can transmit information about the redirected light 1124 to one or more processors 1160 by way of a signal 1132. By way of non-limiting example, the information can include intensity, or radiant flux, or radiant power, or irradiance, or wavelength, or spectral power, or another characteristic. By way of non-limiting example, one or more sensors 1130 can be optical power sensors, photodiodes, phototransistors, spectrometers, or other types of sensors, or any combination thereof. One or more light sources 1120, one or more sensors 1130, and one or more processing units 1160 can be part of a sterilizer 1170 which can be contained within an housing 1172.

An end cap can have a feature or features that can indicate to the user the amount of optical energy at a particular wavelength, or multiple wavelengths, or a range of wavelengths, or multiple ranges of wavelengths that had been transmitted through the end cap in general, or a particular location, or a particular surface, or multiple particular locations or surfaces.

An end cap or end cap assembly can have an indicator 1118 that can change state based on the amount of optical energy at a particular wavelength, multiple wavelengths, a range of wavelengths, or multiple ranges of wavelengths of light, transmitted through the cap in general, or a particular location, or a particular surface, or multiple locations or surfaces. The optical energy transmission state indicator 1118 can be based on materials, substances, components or devices which can change state depending on the instantaneous or accumulated amount of optical energy received. By way of non-limiting example, a material which can change color in response to absorbed light energy, such as a caged dye, or photochromic pigment, or other material or substance, can be embedded within an end cap or end cap assembly in a general way, or at a particular location, or multiple locations, which can change color based upon the amount of ultraviolet light energy that had been absorbed by the dye. In this non-limiting example, the color of the caged dye can indicate to a user if a UV light dose administered to a target location via the end cap or end cap assembly is sufficient to kill microorganisms. By way of further non-limiting example, the color change can be reversible or irreversible. By way of further non-limiting example, the photochromic pigment can be a spiropyran or other photochromic pigment.

Figure 12A:
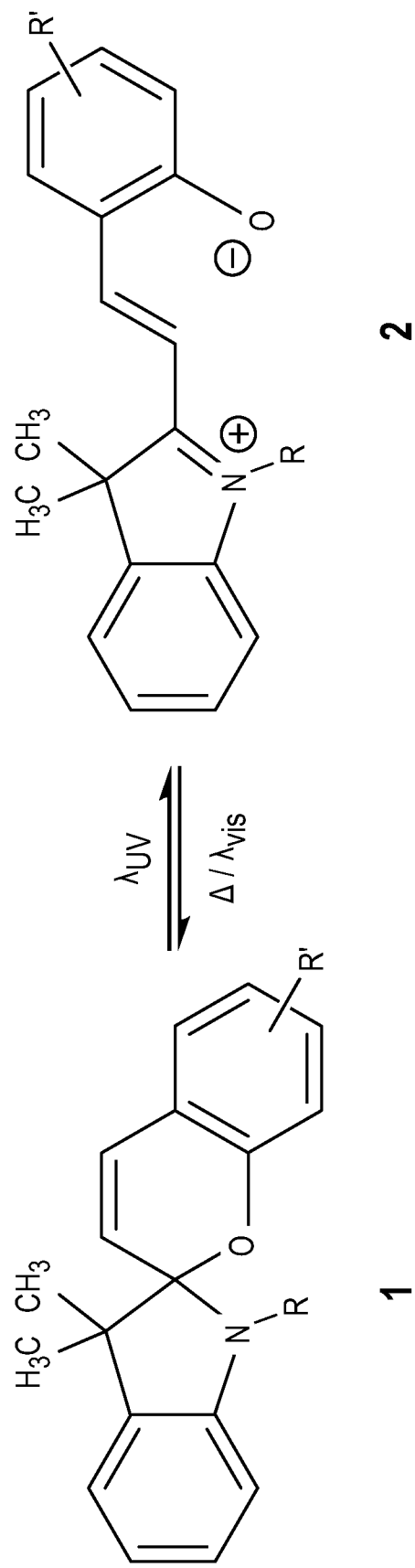
FIG. 12A-I are chemical diagrams of photochromic pigments for use in an energy transmission state indicator, according to an illustrative embodiment.
Figure 12B:
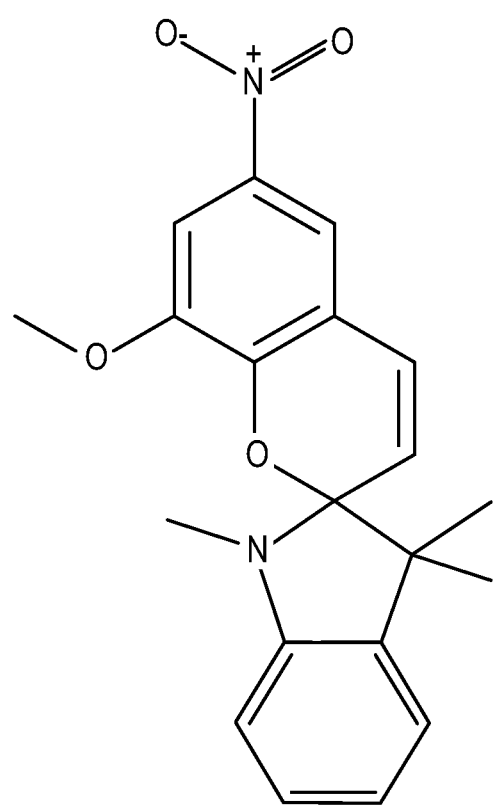
Figure 12C:
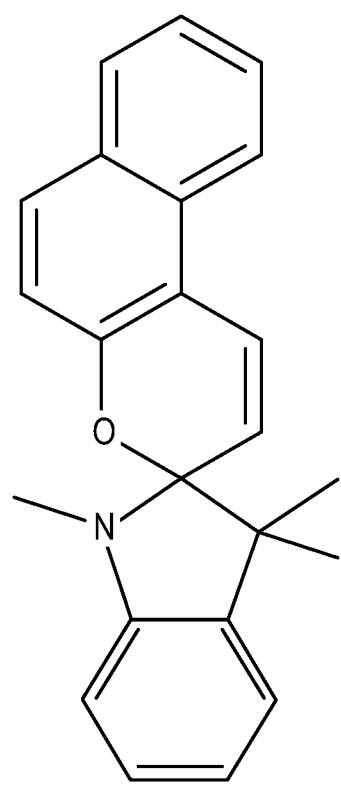
Figure 12D:
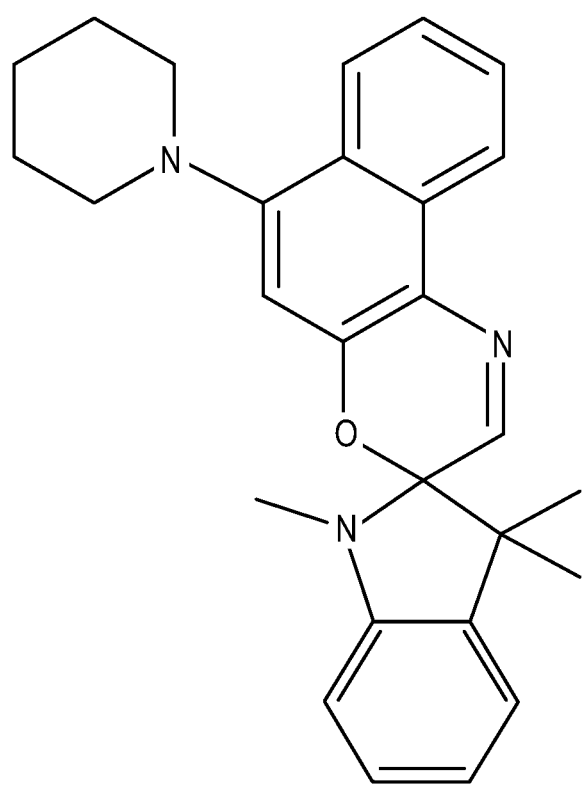
Figure 12E:
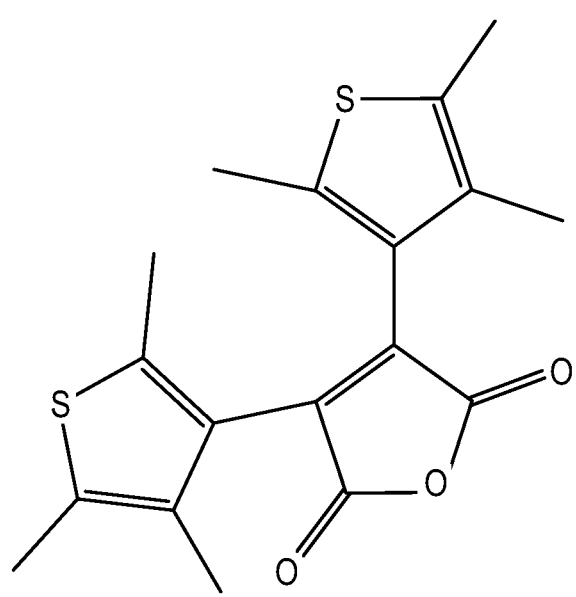
Figure 12F:
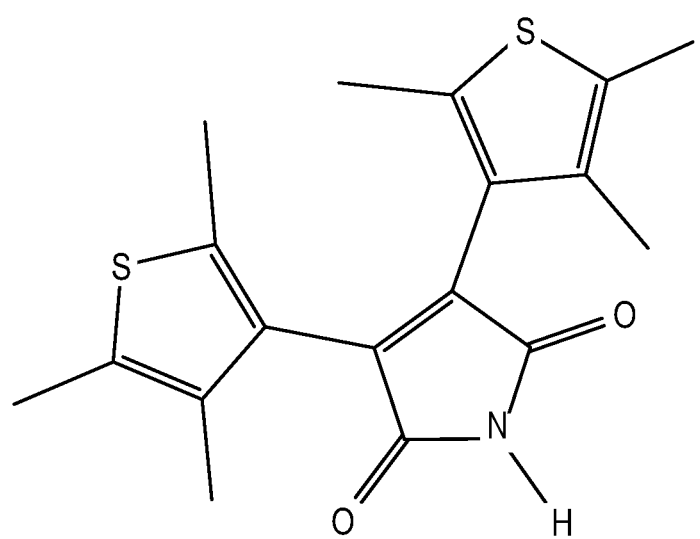
Figure 12G:
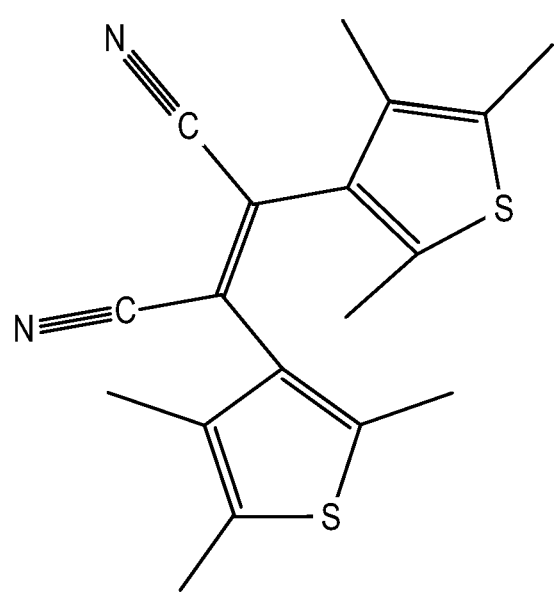
Figure 12H:
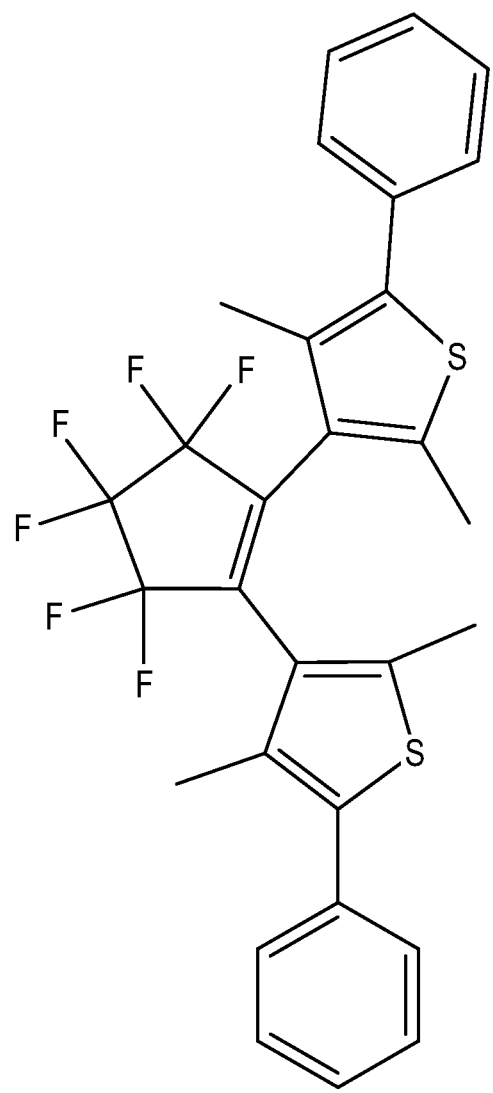
Figure 12I:
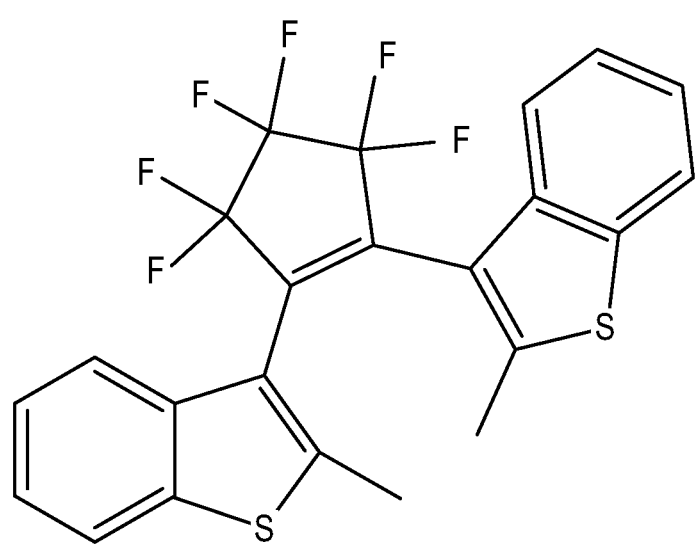

FIG. 12A-I are chemical diagrams of photochromic pigments for use in an energy transmission state indicator, according to an illustrative embodiment. These photochromic pigments can change color when exposed to the sterilizing light. The pigments can be designed so that they require a certain amount of light energy to change color, and they will not change color until they receive the predetermined amount of light energy. In this way, a user can know that when the pigment(s) change color, a sufficient dosage of light has been applied to sterilize the medical device. The pigments can be designed so that they are tuned to respond to a particular wavelength, or wavelengths, or range of wavelengths, or multiple ranges of wavelengths. The pigments can be used to indicate that a sufficient dosage of light has been applied to make the pigments change, and the dosage required to make the pigments change can be calibrated to indicate that a sufficient dosage of light has been applied to sterilize the medical device. A user can see that the color has changed, and can thereby know that enough light has been applied for sterilization. FIG. 12A depicts the reversible transformation of a spiropyran to merocyanine. The spiropyran shown on the right can transform to the merocyanine shown in the left when the spiropyran is exposed to sufficient light energy, and can transform back to the spiropyran under decreased light energy. FIG. 12B-D depict exemplary spiropyrans. FIG. 12B depicts exemplary spiropyran 8-Methoxy-1',3',3'-trimethyl-6-nitrospiro [chromene-2,2'-indole] (PubChem CID 99765). FIG. 12C depicts exemplary spiropyran 1',3',3'-trimethyl-1',3'-dihydrospiro[benzo[f]chromene-3,2'-indole] (PubChem CID 2728827). FIG. 12D depicts exemplary spiropyran 1,3,3-Trimethyl-6'-(piperidin-1-yl)spiro[indoline-2,3'-naphtho[2, 1-b][1,4]oxazine] (PubChem CID 5125966). FIG. 12E-I depict exemplary diarylethenes that can indicate exposure to light of a particular pre-selected wavelength, or wavelengths, or ranges of wavelengths. FIG. 12E depicts exemplary diarylethene 2,3-Bis(2,4,5-Trimethyl-3-Thienyl)Maleic Anhydride (PubChem CID 11382417). FIG. 12F depicts exemplary diarylethene 2,3-Bis(2,4,5-trimethyl-3-thienyl) maleimide (PubChem CID 22023748). FIG. 12G depicts exemplary diarylethene Cis-1,2-Dicyano-1,2-Bis(2,4,5-Trimethyl-3-Thienyl)Ethene (PubChem CID 44630141). FIG. 12H depicts exemplary diarylethene 1,2-Bis(2,4-dimethyl-5-phenyl-3-thienyl)-3,3,4,4,5,5-hexafluoro-1-cyclopentene (PubChem CID 10721339). FIG. 12I depicts exemplary diarylethene 1,2-Bis[2-methylbenzo[b]thiophen-3-yl]-3,3,4,4,5,5-hexafluoro-1-cyclopentene (PubChem CID 11408746).

Figure 13:
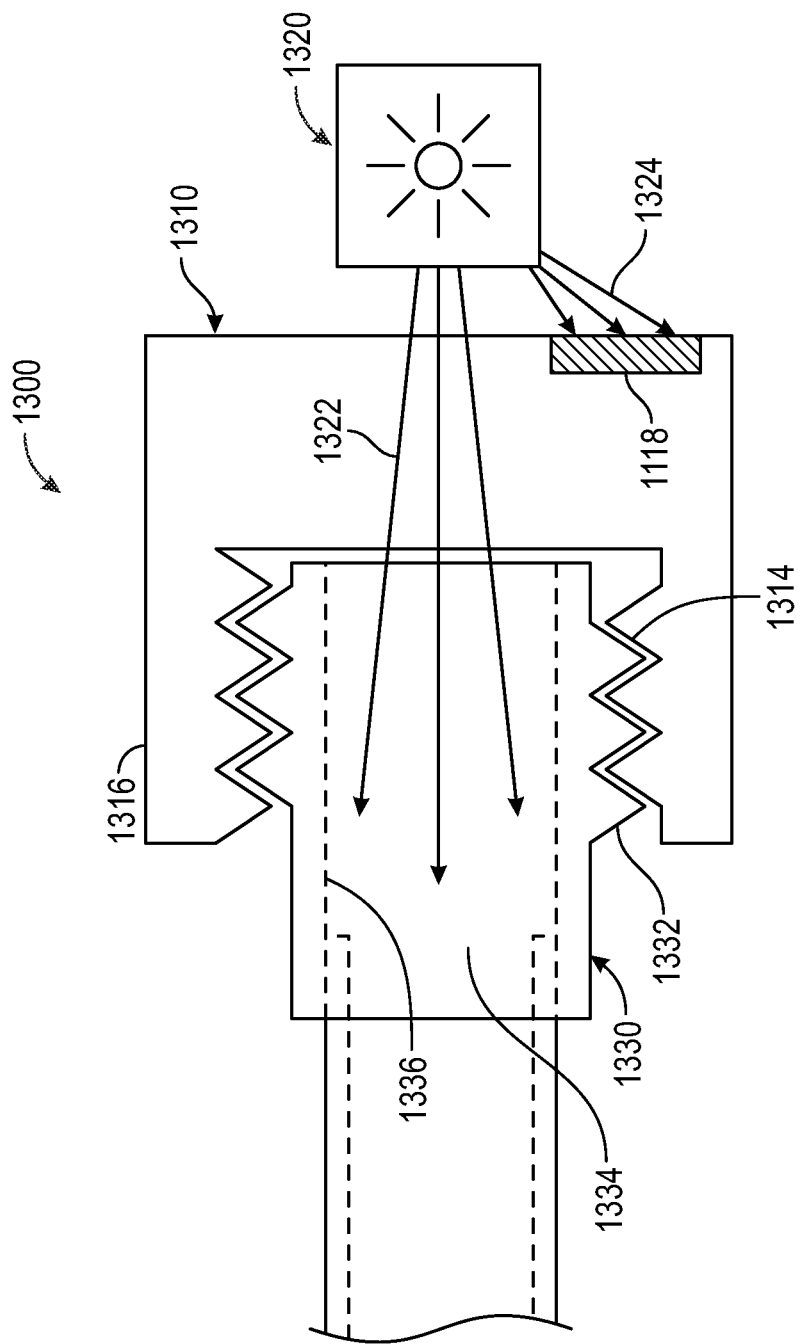
FIG. 13 is a schematic diagram of a sterilization system including an end cap with one or more light-sensing indicators, according to an illustrative embodiment.

FIG. 13 is a schematic diagram of a sterilization system including end cap with one or more light-sensing indicators, according to an illustrative embodiment. A sterilization system can include one or more light emitters 1320. A sterilizing portion of light 1322 can pass through end cap 1310 and be incident upon a medical device 1330, and a detected portion of light 1324 can be incident upon one or more light-sensing indicators 1118 of the end cap 1310. By way of non-limiting example, light-sensing indicators 1118 can be a photochromic substance such as a spiropyran, or a diarylethene, or another type of photochromic substance. In various embodiments, light-sensing indicator 1118 can include an irreversible photoreactive substance. In various embodiments, light sensing indicator 1118 can be a photodiode, or a phototransistor, or an optical power sensor, or another type of electronic sensor. If light-sensing indicator 1118 is a photochromic or irreversible photoreactive chemical substance, it can be incorporated or embedded into the material of the end cap body 1316. In various embodiments, the end cap body material can be an injection-molded plastic and a spiropyran photochromic substance can be mixed with or embedded in the material. If light-sensing indicator 1118 are electronic sensors, they can be embedded within the end cap body 1316 and can transmit signals containing information about the received light.

The sterilizing portion of light 1322 can be transmitted by end cap 1310 to a target 1330. Target 1330 can be a medical device. Target 1330 can have one or more attachment features 1332. The attachment features 1332 can securely attach to corresponding attachment features 1314 of the end cap 1310. The sterilizing portion of light 1322 can irradiate all or part of the target 1330. Target 1330 can have an internal space 1334 and internal sidewalls 1336 that can be sterilized by the sterilizing portion of light 1322.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. By way of non-limiting example, a sterilizer unit can have a housing designed for engagement with an end cap that fits a Luer fitting, or a sterilizer unit can have a housing designed to engage with, or otherwise sterilize, various other devices that can include toothbrushes, contact lenses, or other items that can benefit from sterilization. Various features described herein can be combined and/or rearranged. By way of non-limiting example, a light-coupling end cap can have both a light-sensing part and a mechanical feature which can change the optical transmission properties of an internal or external optical path. A light-coupling end cap can have an optic at a front part and can have a securing feature or features which can enable the end cap to be securely connected to a separate object. A light-coupling end cap can have a body thermally bonded to an optical component and can function within a photointerruptor sensing system. Also, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A sterilizer cap comprising:
   an outer shroud having an inner threaded region;
   an frustoconical shaped inner connector interface disposed at least partially within the outer shroud and defining a hollow inner cavity that is separated from the inner threaded region and that has an open outer end and an inner end configured for engagement with a target medical equipment;
   an optic guide element disposed within the inner cavity defined by the inner connector interface and secured to the inner connector interface thereby sealing the open outer end of the hollow inner cavity from the inner end, the optic guide element controlling a path of light presented at the open outer end for sterilizing the target medical equipment; and
   a photointerrupter system configured to detect engagement to a connector associated with the target medical equipment with respect to the inner connector interface for facilitating sterilization with the sterilizer cap.

2. The sterilizer cap as set forth in claim 1 wherein the outer shroud and the inner connector interface are adapted to interconnect with a medical device.

3. The sterilizer cap as set forth in claim 2 wherein the medical device includes a Luer fitting and the outer shroud is adapted to engage and lock relative the Luer fitting.

4. The sterilizer cap as set forth in claim 2, further comprising one or more light-sensing indicators, that receive light from a sterilization system incident on the medical device.

5. The sterilizer cap as set forth in claim 4 wherein the one or more light-sensing indicators comprise a photochromic substance, an irreversible photoreactive substance, a photodiode, a phototransistor, or an optical power sensor.

6. The sterilizer cap as set forth in claim 5 wherein the photochromic or irreversible photoreactive chemical substance is incorporated or embedded into a material of the sterilizer cap.

7. The sterilizer cap as set forth in claim 1 wherein the optic guide element is operatively connected to a beam splitter that divides light passing through the optic guide element.

8. The sterilizer cap as set forth in claim 1, further comprising, one or more sensors adapted to receive redirected light from the optic guide element and communicate digital information about the redirected light to one or more processors.

9. The sterilizer cap as set forth in claim 8 wherein the information includes at least one of intensity, or radiant flux, or radiant power, or irradiance, or wavelength, and spectral power.

10. The sterilizer cap as set forth in claim 1, further comprising one or more light-sensing indicators, that receive light from a sterilization system incident on a medical device.

11. The sterilizer cap as set forth in claim 10 wherein the one or more light-sensing indicators comprise a photochromic substance, an irreversible photoreactive substance, a photodiode, a phototransistor, or an optical power sensor.

12. The sterilizer cap as set forth in claim 1 wherein the optic guide element is disposed transverse to an engagement axis of the inner connector interface.

13. The sterilizer cap as set forth in claim 1 further comprising a sterilizing radiation monitoring system that disengages a source of sterilizing radiation in response to detecting sterilizing radiation proximal to the inner connector interface that exceeds a safe threshold.

14. The sterilizer cap as set forth in claim 1, wherein the optic guide element is separably secured to the inner connector interface.

* * * * *